United States Patent
Hong et al.

(10) Patent No.: US 10,470,993 B2
(45) Date of Patent: Nov. 12, 2019

(54) TOOTH REMINERALIZATION COMPOSITIONS AND METHODS

(71) Applicant: University of Tennessee Research Foundation, Knoxville, TN (US)

(72) Inventors: Liang Hong, Collierville, TN (US); Linfeng Wu, Cordova, TN (US)

(73) Assignee: University of Tennessee Research Foundation, Knoxville, TN (US)

(*) Notice: Subject to any disclaimer, the term of this patent is extended or adjusted under 35 U.S.C. 154(b) by 0 days.

(21) Appl. No.: 15/042,905

(22) Filed: Feb. 12, 2016

(65) Prior Publication Data

US 2016/0243018 A1  Aug. 25, 2016

Related U.S. Application Data

(63) Continuation-in-part of application No. PCT/US2014/050928, filed on Aug. 13, 2014.

(60) Provisional application No. 61/865,737, filed on Aug. 14, 2013.

(51) Int. Cl.
| | |
|---|---|
| A61K 8/02 | (2006.01) |
| A61Q 11/00 | (2006.01) |
| A61K 8/24 | (2006.01) |
| A61K 33/06 | (2006.01) |
| A61K 8/73 | (2006.01) |
| A61K 8/11 | (2006.01) |
| A61K 8/19 | (2006.01) |
| A61K 31/722 | (2006.01) |

(52) U.S. Cl.
CPC ............ *A61K 8/736* (2013.01); *A61K 8/025* (2013.01); *A61K 8/11* (2013.01); *A61K 8/19* (2013.01); *A61K 8/24* (2013.01); *A61K 31/722* (2013.01); *A61Q 11/00* (2013.01); *A61K 2800/412* (2013.01); *A61K 2800/413* (2013.01); *A61K 2800/592* (2013.01); *A61K 2800/74* (2013.01)

(58) Field of Classification Search
CPC ... A61K 8/00; A61K 8/02; A61K 8/24; A61K 8/025; A61K 8/11; A61K 31/722; A61Q 11/00
See application file for complete search history.

(56) References Cited

U.S. PATENT DOCUMENTS

| | | |
|---|---|---|
| 4,080,440 A | 3/1978 | DiGiulio et al. |
| 4,083,955 A | 4/1978 | Grabenstetter et al. |
| 4,367,218 A | 1/1983 | Jacobson |
| 4,606,912 A | 8/1986 | Rudy et al. |
| 5,571,502 A * | 11/1996 | Winston ............... A61K 8/19 424/49 |
| 5,738,840 A | 4/1998 | Richter et al. |
| 5,833,957 A | 11/1998 | Winston et al. |
| 6,159,448 A | 12/2000 | Winston et al. |
| 7,638,143 B2 | 12/2009 | Piene et al. |
| 9,044,500 B2 | 6/2015 | Kawa et al. |
| 9,161,909 B2 | 10/2015 | Domb et al. |
| 2007/0183984 A1 | 8/2007 | Haas |
| 2007/0196494 A1 | 8/2007 | Grenier et al. |
| 2007/0249733 A1 | 10/2007 | Bae et al. |
| 2008/0075675 A1 | 3/2008 | Reynolds et al. |
| 2010/0330002 A1* | 12/2010 | Robinson ............... A61K 8/64 424/48 |
| 2012/0301408 A1 | 11/2012 | Baker et al. |
| 2013/0164311 A1 | 6/2013 | Decarlo et al. |

FOREIGN PATENT DOCUMENTS

| | | |
|---|---|---|
| FR | 3010635 | 3/2015 |
| WO | 2002017868 A1 | 3/2002 |

OTHER PUBLICATIONS

Sekiguchi et al. Molecular Weight Dependency of Antimicrobial Activity by Chitosan Oligomers, Food Hydrocolloids: Structures, Properties, and Functions, 1994, pp. 71-76.*
Choi et al., In Vitro Antimicrobial Activity of a Chitooligosaccharide Mixture Against Actinobacillus Actinomycetemcomitans and *Streptococcus mutans*, International Journal of Antimicrobial Agents, vol. 18, 2001, pp. 553-557.*
Ruan, Qichao, et al. "An amelogenin—chitosan matrix promotes assembly of an enamel-like layer with a dense interface." Acta Biomaterialia. vol. 9. Iss. 7. Apr. 2013: 7289-7297.
International Search Report and Written Opinion of the International Searching Authority (US), dated Nov. 14, 2014 of International Patent Application No. PCT/US2014/050928, filed Aug. 13, 2014.
Hurlbutt, et al. "Dental Caries: A pH-mediated disease." CDHA Journal—Winter 2010; pp. 9-15.
International Search Report and Written Opinion of the International Searching Authority dated Jun. 6, 2014 of International PCT Application No. PCT/US2014/019447 filed Feb. 28, 2014.

* cited by examiner

*Primary Examiner* — Lezah Roberts
(74) *Attorney, Agent, or Firm* — Sorell, Lenna & Schmidt, LLP; William D. Schmidt, Esq.

(57) ABSTRACT

Tooth remineralization compositions are provided for preventing and treating tooth decay and dental erosion in a patient. The composition comprises a remineralizing agent encapsulated in a polymer. In various embodiments, the remineralizing agent may be in a polymeric chitosan microspheres and/or nanospheres and the remineralizing agent comprises calcium and/or phosphate. Methods of preparation and use of the remineralization compositions are also disclosed.

12 Claims, 14 Drawing Sheets

TOOTH REMINERALIZATION COMPOSITIONS AND METHODS

This application is a continuation in part of PCT/US2014/050928, filed on Aug. 13, 2014, entitled "TOOTH REMINERALIZATION COMPOSITIONS AND METHODS," which claims the benefit of the filing date of Provisional Application No. 61/865,737, filed Aug. 14, 2013, entitled "TOOTH REMINERALIZATION COMPOSITIONS AND METHODS". These entire disclosures are hereby incorporated by reference into the present disclosure.

BACKGROUND

The present application relates to methods and compositions for remineralization of the teeth due to mineral loss related dental conditions such as dental caries and/or dental erosion.

Dental caries (tooth decay) is a prevalent chronic disease affecting 60% to 90% of school-aged children in industrialized countries and the vast majority of adults. It is a significant cause of hospital admissions, emergency department care and the use of general anesthetics among young children. In the United States, dental caries is the single, most common chronic disease of childhood. Its prevalence (59%) among children is 5 times more common than asthma (11%) and 7 times more common than hay fever (8%). (US Department of Health and Human Services. Oral Health in America: A Report of the Surgeon General. (2000)). The National Health and Nutrition Examination Survey (NHANES) 1999-2004 data showed that 28% of 2-5 year olds in the U.S. have caries in their primary teeth and the prevalence increased by 15% during the last decade. (CDC Morbidity and Mortality Weekly Report 54, 1-44 (2005), Dye, B. A. et al. Trends in oral health status: United States, 1988-1994 and 1999-2004. Vital Health Stat 11, 1-92 (2007)). The treatment of dental caries is expensive, representing roughly 60% of annual dental health care costs and averaging 6% of total and 16% of private healthcare expenditure in developed countries. (Organization for Economic Co-operation and Development (OECD). Health at a Glance, 2009: OECD Indicators. (2009).)

Childhood dental caries often goes untreated; thereby exacerbating the problem and leading to many serious co-morbidities, including chronic pain, tooth loss, difficulty hearing, eating, speaking, sleeping, and failure to thrive, as well as poor school performance, social relationships, and self-image, and decreased success later in life. Because of disease burden, co-morbidities, and negative social consequences, dental caries has become a focal issue in efforts to reduce public health disparities for both NIDCR and the American Academy of Pediatrics. Over the past 40 years, fluoride has been the cornerstone for caries prevention. Also during that time, the number of different sources of fluoride has increased and now includes a variety of sources, such as fluoride dentifrices, fluoride gel, and other therapeutic fluoride products. Even with such a high availability, the caries-preventive effect of fluoride use has been leveled off and the prevalence of mild dental fluorosis has significantly increased during the last several decades. Fluoride toothpaste is most widely used fluoride modality, but conventional fluoride toothpaste has a significant caries-preventive effect only at concentrations of 1,000 parts per million (ppm) or higher. However this concentration of toothpaste is associated with an increased risk of fluorosis when used by young children under the age of 6, particularly before two years old. The first two years of life has been identified as most important to fluorosis development for early-erupting permanent teeth, such as incisors and first molars. (Hong, L., Levy, S. M., Warren, J. J., Broffitt, B. & Cavanaugh, J. Fluoride intake levels in relation to fluorosis development in permanent maxillary central incisors and first molars. *Caries Res* 40, 494-500 (2006). Hong, L. et al. Timing of fluoride intake in relation to development of fluorosis on maxillary central incisors. *Community Dent Oral Epidemiol* 34, 299-309 (2006).) Thus, the anti-caries effect of traditional fluoride therapy has a limitation.

Non-fluoride topical remineralizing agents containing calcium and/or phosphate has been investigated and showed the potential as an alternative to fluoride or as an adjunct to fluoride to enhance its effectiveness at lower fluoride concentration. Such agents would be of particular benefit to children to reduce the risk of fluorosis as well as to prevent caries. Casein Phosphoprotein-amorphous calcium phosphate (CPP-ACP) is currently most commonly used in clinic. Although there is substantial laboratory and in situ evidence for a benefit, recent review of current clinical trial data by the American Dental Association (ADA) Council on Scientific Affairs (CSA) reported that the evidence is weak and insufficient to support recommending any of the current mineral formulations for caries reduction, including CPP-ACP based products (Rethman, M. P. et al. Nonfluoride caries-preventive agents: executive summary of evidence-based clinical recommendations. J Am Dent Assoc 142, 1065-1071 (2011)). Calcium-Phosphate (Ca—P) compounds have been added to a variety of topical delivery vehicles and are commercially available in toothpaste, chewing gum, varnish, and mouth rinse. (Zero, D. T. Dentifrices, mouthwashes, and remineralization/caries arrestment strategies. BMC Oral Health 6 Suppl 1, S9 (2006)). The significant problem with CPP-ACP is its low solubility in acidic microenvironment where tooth demineralization occurs. The problem of stabilizing calcium and phosphate ions so that bioavailable Ca—P can be delivered when needed is a major challenge which impedes a large scale, population-based utilization of Ca—P-based products for caries prevention and control. Thus CPP-ACP products cannot deliver fresh ACP quickly at an adequate level for remineralization when the tooth is attacked by the acids produced by oral bacteria. There is a continued need to search for a better delivery system of calcium and phosphate to the teeth.

Accordingly, there is a need for compositions and methods to prevent and treat dental erosion and/or dental caries in patients exhibiting dental erosion and/or dental caries, especially in children. Additional and more effective compositions and methods are needed to remineralize the teeth. Patients suffering from dental erosion and or dental caries are in urgent need of alternatives to fluoride therapy.

SUMMARY

New compositions and methods are provided that effectively prevent and treat dental erosion and/or dental caries in patients suffering from these mineral-loss dental conditions. Additionally, new compositions and methods are provided that are alternatives to fluoride therapy for the remineralization of teeth.

In one embodiment, a composition is provided for remineralizing the teeth, the composition comprising a remineralizing agent encapsulated in a polymer.

In an exemplary embodiment, the remineralizing agent is in polymeric microspheres and/or nanospheres and the polymer is a natural biopolymer comprising chitosan.

In another exemplary embodiment, the composition is a toothpaste, gel, varnish, cream, sealant and/or chewing gum.

In another embodiment, the composition comprises from about 1% to about 10% by weight calcium phosphate based on the total weight of the composition.

In another embodiment, the remineralizing agent comprises calcium and/or phosphate having a particle size from 1 μM to about 250 μM or from 1 μM to about 100 μM.

In an exemplary embodiment, the composition comprises microsphere which comprise chitosan and calcium, or chitosan and phosphate, or a mixture thereof or the composition comprises a first set of microspheres comprising calcium; and/or a second set of microspheres comprising phosphate.

In yet another embodiment, the microspheres comprising calcium and the microspheres comprising phosphate are mixed at a ratio of between about 1:1 to about 1:2 of calcium to phosphate.

In another embodiment, the microspheres comprising calcium and the microspheres comprising phosphate degrade and form amorphous calcium phosphate in situ in an aqueous environment in the oral cavity. The calcium phosphate then can provide the source of calcium ions and phosphate ions to the teeth.

In another embodiment, the composition further comprises fluoride salts and/or xylitol. In some embodiments, the composition further comprises salts comprising calcium acetate, $CaCl_2$, calcium pantothenate, calcium ascorbate, calcium gluconate, calcium lactate, calcium acetylacetonate, calcium lactobionate, calcium citrate, calcium α-D-heptagluconate, calcium benzoate, saccharin calcium and/or sorbic acid calcium.

In one embodiment, a method is provided for treating or preventing dental erosion, the method comprising applying a therapeutically effective amount of a remineralizing agent encapsulated in a polymer to the teeth, wherein the remineralizing agent is calcium and/or phosphate and the polymer is chitosan.

In another embodiment, the remineralizing agent is encapsulated in a microsphere and/or a nanosphere.

In another embodiment, the chitosan microsphere comprises chitosan and calcium, or chitosan and phosphate, or a mixture thereof.

In one embodiment, an antimicrobial composition is provided for use in the oral cavity, the composition comprising chitosan having a molecular weight of about 1 kilodalton to about 10 kilodaltons.

In another embodiment, the chitosan has a molecular weight of about 1 kilodalton to about 10 kilodaltons.

In another embodiment, a method of increasing antimicrobial activity of an oral composition is provided, the method comprising adding to the composition chitosan having a molecular weight of about 1 kilodalton to about 10 kilodaltons.

In yet another embodiment, a method of making an oral composition for remineralizing teeth is provided, the method comprising encapsulating calcium in a first set of chitosan microspheres, encapsulating phosphate in a second set of chitosan microspheres and combining the first set of microspheres with the second set of microspheres.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

DETAILED DESCRIPTION

Figure 1:
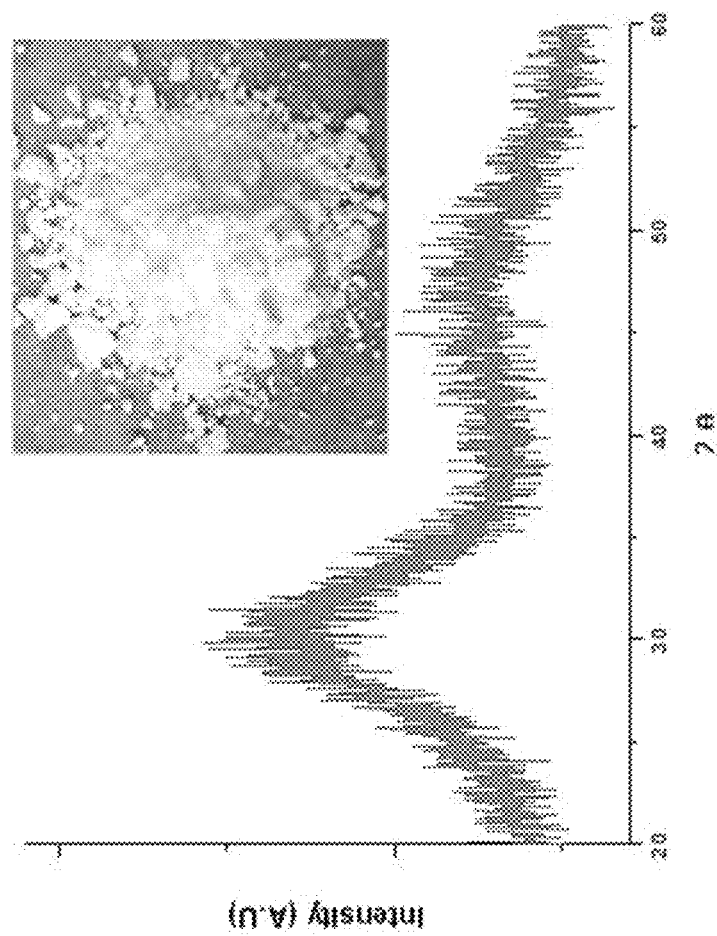
FIG. 1 illustrates the X-ray diffraction pattern of hybrid chitosan amorphous calcium phosphate and its physical appearance.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application to the doctrine of equivalents for the scope of the claims, each numerical parameter should at least be construed in light of the number of reported significant digits and by applying ordinary rounding techniques.

Notwithstanding that the numerical ranges and parameters setting forth, the broad scope of the application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a remineralizing agent" includes one, two, three or more remineralizing agents.

Reference will now be made in detail to certain embodiments of the application, examples of which are illustrated in the accompanying drawings. While the application will be described in conjunction with the illustrated embodiments, it will be understood that they are not intended to limit the application to those embodiments. On the contrary, the application is intended to cover all alternatives, modifications, and equivalents, which may be included within the application as defined by the appended claims.

The headings below are not meant to limit the disclosure in any way; embodiments under any one heading may be used in conjunction with embodiments under any other heading.

Definitions

The terms "treating" and "treatment" include "preventing" or "prevention" of disease or undesirable condition. In addition, "treating" or "treatment" does not require complete alleviation of signs or symptoms, does not require a cure, and specifically includes protocols that have only a marginal effect on the patient. "Reducing caries" includes a decrease in caries and does not require complete alleviation of caries signs or symptoms, and does not require a cure. "Reducing erosion" includes a decrease in erosion and does not require complete alleviation of erosion signs or symptoms, and does not require a cure.

A "therapeutically effective amount" or "effective amount" is such that when administered, the remineralizing agent results in alteration of the effects of acid in the oral cavity, such as, for example, prevention of dental erosion or tooth decay or reduction of dental erosion, re-hardening and remineralization of tooth enamel, etc.

The term "remineralization" is a natural process in which a tooth's minerals are restored or replaced. Remineralization reverses the process of decay and/or erosion caused from demineralization.

The term "encapsulated" refers to enclosing a composition via a protective coating and/or membrane. In some embodiments, the membrane is a biodegradable polymeric matrix.

The term "carrier" refers to any vehicle that is pharmaceutically acceptable and can be used to apply the present compositions in the oral cavity.

The term "polymer" refers to polysaccharides, such as starch, cellulose, chitine, chitosan, or alginic acid; polypeptides of natural origin, such as gelatin; polymers having carbon backbones, such as polyvinyl alcohol and polyvinyl acetate; and polymers having a hydrolyzable backbone, such as polylactide, poly(lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide), polycaprolactones, polyamides, polyurethanes, polyanhydrides and poly(amide-enamines). Some commonly used biodegradable polymers are co-polymers, which are composed of various combinations and variations of hydrolysable polymers.

The term "biodegradable polymer", as used herein, refers to a polymer that at least a portion thereof, as defined hereinabove, decomposes under physiological conditions. The polymer can thus be partially decomposed or fully decomposed under physiological conditions including the physiological conditions in the mouth.

The term "composition" can take any form suitable for application to an oral surface. In various embodiments, the composition can be a liquid solution suitable for irrigating, rinsing or spraying; a dentifrice such as a powder, toothpaste or dental gel; a periodontal gel; a liquid suitable for painting a dental surface (e.g., a liquid whitener); a chewing gum; a dissolvable, partially dissolvable or non-dissolvable film or strip (e.g., a whitening strip); an encapsulate (e.g., composition encapsulated in gelatin and/or a polymer), a wafer; a lozenge, a wipe or towelette; an implant; a mouthrinse, a foam, a dental floss; etc. The composition can contain active and/or carrier ingredients additional to those recited above.

The term "preventing" or "prevents" refers to executing a protocol, which may include administering one or more compositions to a patient (human or otherwise), in an effort to stop or delay symptoms of a disease and/or a condition.

The section headings below are not meant to limit the application and one section heading can be interchanged with any other section heading.

Tooth Decay and Dental Erosion

Dental caries (tooth decay) is one of the most common chronic diseases worldwide. It is typically caused by a bacterial infection which leads to demineralization and destruction of the tooth enamel and dentin. Dental caries affects 60% to 90% of school-aged children in industrialized countries and the vast majority of adults. (Organization for Economic Co-operation and Development (OECD). Health at a Glance, 2009: OECD Indicators. (2009)). Data from one report showed that 28% of 2-5 year olds in the U.S. have caries in their primary teeth and the prevalence increased by 15% during last decade. (US Department of Health and Human Services. Oral Health in America: A Report of the Surgeon General. (2000). CDC Morbidity and Mortality Weekly Report 54, 1-44 (2005)).

Dental erosion is an irreversible loss of tooth minerals by a chemical process without bacterial involvement. It can occur in primary and permanent dentitions, and can affect any tooth surface with the facial, occlusal, and lingual tooth surfaces most involved (Bartlett D W, Shah P. A critical review of non-carious cervical lesions and the role of abfraction, erosion, and abrasion. J Dent Res 2006; 85 (4): 306-12. Williams D, Croucher R, Marcenes W, O'Farrell M. The prevalence of dental erosion in the maxillary incisors of 14-year old school-children living in Tower Hamlets and Hackney, London, UK. Int Dent J 1999; 49 (4): 211-6).

Erosive lesions can be caused by intrinsic or extrinsic acids which may lead to irreversible damage to the dentition. Initially, the tooth surface softens due to loss of calcium and phosphate, but eventually there will be an apparent loss of tooth structure. The clinical appearance of dental erosion includes broad concavities on smooth surface enamel and increased incisal translucency, which can have undesirable esthetic implications. Furthermore, loss of enamel can lead to dentin exposure and hypersensitivity, even progressing as far as pulp exposure in some extreme cases.

Epidemiological studies of dental erosion have reported 46% of children aged 13-19 years had dental erosion on at least one tooth with maxillary teeth being more prevalent (McGuire J, Szabo A, Jackson S, Bradley T. G., Okunseri C. Erosive tooth wear among children in the United States: relationship to race/ethnicity and obesity. Int J Ped Dent 2009; 19 (2): 91-8.) Dental erosion has become a growing concern in developed countries (Nunn J. Prevalence of dental erosion and the implication for oral health. Eur J Oral Sci 1996; 104 (2): 156-161). Due to the increased consumption of carbonated soft drinks and fruit juice, its prevalence and severity is expected to continue increasing.

Many risk factors have been identified in past studies on erosion. For example, certain medical conditions like vomiting with bulimia or anorexia, along with regurgitation in gastro-esophageal reflux disease. Binge drinking with alcoholics could cause dental erosion. Certain medications which have ascorbic, liquid hydrochloric or acetylsalicylic acids could also cause dental erosion. Excessive overall consumption or increased frequency of consumption of acidic fruits, pure fruit juices and acidic drinks. Other potential risk factors include person's occupation and illegal drug use.

Studies have documented that dental erosion is the major cause of tooth wear in children (Dugmore C, & Rock W. A multifactorial analysis of factors associated with dental erosion. Br Dent J 2004; 196 (5): 283-6). Significance of preventing and treating dental erosion at an early stage is of utmost importance. Dental erosion is an irreversible process, and therefore must be carefully evaluated for in each visit. The condition is irreversible, and it may continue unchecked into adulthood unless the causes are addressed. Significant tooth structure loss may require more extensive dental treatment or possible extraction. Therefore, prevention and treatment of dental erosion at a young age is crucial.

Dental erosion can occur in primary and permanent dentitions, and can affect any tooth surface with the facial, occlusal, and lingual tooth surfaces most involved (Bartlett D W, Shah P. A critical review of non-carious cervical lesions and the role of abfraction, erosion, and abrasion. J Dent Res 2006; 85 (4): 306-12. Williams D, Croucher R, Marcenes W, O'Farrell M. The prevalence of dental erosion in the maxillary incisors of 14-year old school-children living in Tower Hamlets and Hackney, London, UK. Int Dent J 1999; 49 (4): 211-6).

Therefore, there is a need for compositions and methods to prevent and treat dental erosion in patients exhibiting dental erosion, especially in children. Additional and more effective compositions and methods are needed to remineralize the teeth. Patients suffering from dental erosion are in urgent need of remineralization therapy. Loss of enamel can lead to dentin exposure and hypersensitivity, even progressing as far as pulp exposure in some extreme cases.

Remineralization

Remineralization is encouraged to prevent and treat dental caries. Remineralization occurs when a mineral is added to the teeth to replace mineral components that have been depleted from the teeth. One of the most common remineralizing agents is fluoride. There are several other remineralizing agents, including Amorphous Calcium Phosphate (ACP), tricalcium phosphate, Casein Phosphoprotein-ACP, bioactive glass-calcium sodium phosphosilicate, and Arginine bicarbonate-calcium carbonate complex. Yet, other examples of remineralization agents include calcium, and/or phosphate or combinations thereof. Calcium Phosphate (Ca—P)-based remineralizing products as non-fluoride caries preventive agents can deliver calcium and phosphate ions in bioavailable forms and at sufficient concentrations to tooth surface to drive remineralization. However, recent clinical trial data suggest that there is a need for more efficient delivery of Ca—P products for sufficient reduction of dental caries.

In one embodiment of the present application, a composition is provided for remineralizing teeth, said composition comprising a remineralizing agent. In some embodiments, the remineralizing agent comprising calcium is obtained from calcium chloride, calcium phosphate, amorphous calcium phosphate or combinations thereof. In some embodiments, the remineralizing agent comprising phosphate is obtained from sodium phosphate, potassium phosphate, casein phosphopeptide, caseinates, digests thereof or casein-derived phosphopeptides, amorphous calcium phosphate or combinations thereof. In some embodiments, remineralizing agents are added to the composition at a concentration of about 0.001% to about 10% w/w, w/v, or v/v.

In various embodiments, remineralizing agents are added to the composition at a concentration of about 0.001%, 0.005, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.0, 2.05, 2.10, 2.15, 2.20, 2.25, 2.30, 2.35, 2.40, 2.45, 2.50, 2.55, 2.60, 2.65, 2.70, 2.75, 2.80, 2.85, 2.90, 2.95, 3.0, 3.05, 3.10, 3.15, 3.20, 3.25, 3.30, 3.35, 3.40, 3.45, 3.50, 3.55, 3.60, 3.65, 3.70, 3.75, 3.80, 3.85, 3.90, 3.95, 4.0, 4.05, 4.10, 4.15, 4.20, 4.25, 4.30, 4.35, 4.40, 4.45, 4.50, 4.55, 4.60, 4.65, 4.70, 4.75, 4.80, 4.85, 4.90, 4.95, 5.0, 5.05, 5.10, 5.15, 5.20, 5.25, 5.30, 5.35, 5.40, 5.45, 5.50, 5.55, 5.60, 5.65, 5.70, 5.75, 5.80, 5.85, 5.90, 5.95, 6.0, 6.05, 6.10, 6.15, 6.20, 6.25, 6.30, 6.35, 6.40, 6.45, 6.50, 6.55, 6.60, 6.65, 6.70, 6.75, 6.80, 6.85, 6.90, 6.95, 7.0, 7.05, 7.10, 7.15, 7.20, 7.25, 7.30, 7.35, 7.40, 7.45, 7.50, 7.55, 7.60, 7.65, 7.70, 7.75, 7.80, 7.85, 7.90, 7.95, 8.0, 8.05, 8.10, 8.15, 8.20, 8.25, 8.30, 8.35, 8.40, 8.45, 8.50, 8.55, 8.60, 8.65, 8.70, 8.75, 8.80, 8.85, 8.90, 8.95, 9.0, 9.05, 9.10, 9.15, 9.20, 9.25, 9.30, 9.35, 9.40, 9.45, 9.50, 9.55, 9.60, 9.65, 9.70, 9.75, 9.80, 9.85, 9.90, 9.95 and 10.0% w/w, w/v, or v/v.

In some embodiments, the remineralizing agent is encapsulated in a polymer. In some embodiments, this allows the calcium and the phosphate to be separate from each other and stabilizes the composition. When the calcium and the phosphate contact the oral environment, the calcium and the phosphate will come in contact with each other and form amorphous calcium phosphate allowing a source of calcium ions and phosphate ions to contact the teeth and aid in remineralization. In some embodiments, the polymer comprises chitosan. In other embodiments, the polymer comprises a nanosphere and/or a microsphere. The remineralizing agent is encapsulated in the polymeric microsphere at a concentration of about 0.001% to 7.5% or from about 0.01% to about 1%, or from about 0.05% to about 2%, about 2% to about 5% w/w, w/v, or v/v.

In various embodiments, the remineralizing agent is encapsulated in the polymeric microsphere at a concentration of about 0.001%, 0.005, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.0, 2.05, 2.10, 2.15, 2.20, 2.25, 2.30, 2.35, 2.40, 2.45, 2.50, 2.55, 2.60, 2.65, 2.70, 2.75, 2.80, 2.85, 2.90, 2.95, 3.0, 3.05, 3.10, 3.15, 3.20, 3.25, 3.30, 3.35, 3.40, 3.45, 3.50, 3.55, 3.60, 3.65, 3.70, 3.75, 3.80, 3.85, 3.90, 3.95, 4.0, 4.05, 4.10, 4.15, 4.20, 4.25, 4.30, 4.35, 4.40, 4.45, 4.50, 4.55, 4.60, 4.65, 4.70, 4.75, 4.80, 4.85, 4.90, 4.95, 5.0, 5.05, 5.10, 5.15, 5.20, 5.25, 5.30, 5.35, 5.40, 5.45, 5.50, 5.55, 5.60, 5.65, 5.70, 5.75, 5.80, 5.85, 5.90, 5.95, 6.0, 6.05, 6.10, 6.15, 6.20, 6.25, 6.30, 6.35, 6.40, 6.45, 6.50, 6.55, 6.60, 6.65, 6.70, 6.75, 6.80, 6.85, 6.90, 6.95, 7.0, 7.05, 7.10, 7.15, 7.20, 7.25, 7.30, 7.35, 7.40, 7.45 and/or 7.50% w/w, w/v, or v/v.

In various embodiments, the particle size of the remineralizing agent is from about 1 µm to about 100 µm or from about 5 µm to about 100 µm or from about 100 µm to about 200 µm or from about 1 µm to about 200 µm. In various embodiments, the particle size of the remineralizing agent is from about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 and/or 200 µm.

In some other embodiments, the particle size of the polymeric microsphere is from about 1 µm to about 500 µm or from about 10 µm to about 100 µm or from about 10 µm to about 500 µm. In various embodiments, the particle size of the polymeric microsphere is from about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495 and/or 500 µm.

In some embodiments, the composition comprises a microsphere comprising chitosan and calcium, or a microsphere comprising chitosan and phosphate. The composition further comprises a first microsphere and a second microsphere.

In various embodiments, the microspheres comprising calcium and the microspheres comprising phosphate are mixed at a ratio of between about 1:1 to about 1:2 of calcium to phosphate. In various embodiments, the microspheres comprising calcium and the microspheres comprising calcium and the microspheres comprising phosphate are mixed at a ratio of between about 1:1, 1:2, 1:3, 1:4, 4:1, 3:1 and/or 2:1.

The composition of the present application may be in the form selected from a toothpaste, gel, varnish, mouth rinse or sealant. In one embodiment, the composition is a toothpaste. In some embodiments, the microsphere comprising calcium and the microsphere comprising phosphate are physically separated in the composition in a non-aqueous environment. Thus, the chitosan microsphere comprising calcium and the chitosan microsphere comprising phosphate stabilize the calcium and the phosphate ions so that bioavailable Ca—P can be delivered.

The microsphere comprising calcium and the microsphere comprising phosphate degrade and form amorphous calcium phosphate in situ in an aqueous environment in the oral cavity. The amorphous calcium phosphate forms at a pH of about 1 to 10, or from about 1 to 6, or from about 5 to 10. In some embodiments, the amorphous calcium phosphate forms at a pH of about 1, 2, 3, 4, 5, 6, 7, 8, 9 or 10. The amorphous calcium phosphate provides a source of calcium ions and phosphate ions in situ that penetrate the teeth and aids in their remineralization.

In other embodiments, a method is provided for treating or preventing tooth decay or erosion, the method comprising applying a therapeutically effective amount of a remineralizing agent encapsulated in a polymer to the teeth.

In other embodiments, a method of making an oral composition for remineralizing teeth is provided. The method comprises encapsulating calcium in a first set of chitosan microspheres, encapsulating phosphate in a second set of chitosan microspheres and combining the first set of microspheres with the second set of microspheres.

The present composition comprises chitosan and ACP with each component delivering distinctive but complimentary/synergetic benefits for caries prevention. ACP is a solid solution and is transformed to apatite readily. The present composition provides rapid delivery of fresh calcium and phosphate ions to the microenvironment of demineralized tooth surface through in situ ACP technology. It provides freshly formed in situ ACP which provides ample Ca—P for deep penetration to the body of the lesion. The advantages of ACP compared to other Ca—P compounds include fast formation rate, fast dissolution rate, high solubility, rapid transformation to apatite, and small particle size for deep penetration. The present application also provides a composition for remineralizing teeth that is safe and biocompatible. Young children (age 2 or below) are safe to swallow some toothpaste during tooth-brushing as many of them actually do.

The chitosan-calcium phosphate hybrid complex has a buffering effect to neutralize acid pH microenvironment. The two-microsphere system, in which calcium and phosphate ions are physically separated by encapsulating into separate chitosan microspheres, has distinctive delivery efficacy and stability which is important for a prolonged shelf time. In various embodiments, the chitosan-calcium phosphate hybrid complex has a shelf life of about 6 months to about 2 years. In some embodiments, the chitosan-calcium phosphate hybrid complex has a shelf life of 6, 7, 8, 9, 10, 11, 12, 13, 14, 15, 16, 17, 18, 19, 20, 21, 22, 23 or 24 months.

Chitosan

Chitosan is a derivative of chitin and a natural stabilization biopolymer of calcium and phosphate for exoskeletons of arthropods such as crustaceans (e.g., crabs, lobsters and shrimps). It is polysaccharides with high biocompatibility, biodegradability, and natural antibacterial property. Chitosan is used in food industry as a microbial inhibitor as well as a carrier for delivering calcium and phosphate ions. Unlike synthesized chemical drugs, chitosan is a safe antimicrobial and avoid bacterial resistance. In the present application, chitosan microspheres are used as a delivery system to encapsulate calcium and phosphate ions in separate microspheres. During tooth-brushing, abundant in situ fresh ACP forms and Ca—P easily precipitates to the demineralized hydroxyapatite crystallite surfaces and enhances homogenous remineralization throughout the body of a lesion (subsurface lesion). The chitosan which has a bioadhesive property forms a polymer film on tooth surface and serve as reservoir for ACP and thus extends remineralization. Chitosan can prevent dental erosion and/or dental caries through effectively inhibiting bacteria that causes dental erosion and/or dental caries. This also is particularly so with high molecular weight chitosan.

In one embodiment, an antimicrobial composition is provided for use in the oral cavity. The composition further comprises chitosan having a molecular weight about 1 kilodalton to about 10 kilodaltons, or 2 kilodaltons to about 5 kilodaltons, or about 5 kilodaltons to about 10 kilodaltons. In various embodiments, the composition further comprises chitosan having a molecular weight of about 1, 2, 3, 4, 5, 6, 7, 8, 9 and/or 10 kilodaltons.

In some embodiments, high molecular weight chitosan is more stable at a pH at or below 5, while low molecular weight chitosan is less stable at a pH at or below 5. In some embodiments, the pH range of an acidic environment can be from about 2 to about 6. In various embodiments, the low molecular weight range chitosan is from about 1 kilodalton to about 10 kilodaltons. In some embodiments, the high molecular weight chitosan is from about 100 kilodaltons to about 200 kilodaltons.

In various embodiments, the composition further comprises chitosan having a molecular weight of about 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 and/or 200 kilodaltons.

In some embodiments, the MW range for chitosan can be from about 100-200 kilodaltons. The pH range for chitosan for it to be stable can be from about 2 to about 6. Chitosan is a weak base (basic in nature) so an acidic environment will aid its dissolution and delivery of it to the teeth. Lower MW chitosan is water soluble so it does not need a low pH value for dissolution. For dental caries and dental erosion, these conditions occur when the pH value in oral cavity decreases below about pH 5, whether by bacteria or a chemical acid. In some embodiments, the larger MW chitosan (e.g., from about 1000 to about 5,000 KD or from about 2000 to about 4,000 KD) can be used for these oral conditions.

In various embodiments, the antimicrobial composition reduces and/or inhibits bacterial growth by about 10 to about 95%. In various embodiments, the antimicrobial composition reduces and/or inhibits bacterial growth by 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 or 95%.

In various embodiments, a method is provided for increasing the antibacterial activity in the oral cavity. The method further comprises administering chitosan having a molecular weight about 1 kilodalton to about 10 kilodaltons, or 2 kilodaltons to about 5 kilodaltons, or about 5 kilodaltons to about 10 kilodaltons. In some embodiments, the method further comprises chitosan having a molecular weight about 1, 2, 3, 4, 5, 6, 7, 8, 9 and/or 10. In some embodiments, the chitosan is applied to the oral cavity at a concentration of about 0.1 mg/mL to about to about 5 mg/mL or from about 1 mg/mL to about 3 mg/mL or from about 1 mg/mL to about 5 mg/mL. In various embodiments, the chitosan is applied to the oral cavity at a concentration of about 0.1, 0.5, 1.0, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.0, 2.05, 2.10, 2.15, 2.20, 2.25, 2.30, 2.35, 2.40, 2.45, 2.50, 2.55, 2.60, 2.65, 2.70, 2.75, 2.80, 2.85, 2.90, 2.95, 3.0, 3.05, 3.10, 3.15, 3.20, 3.25, 3.30, 3.35, 3.40, 3.45, 3.50, 3.55, 3.60, 3.65, 3.70, 3.75, 3.80, 3.85, 3.90, 3.95, 4.0, 4.05, 4.10, 4.15, 4.20, 4.25, 4.30, 4.35, 4.40, 4.45, 4.50, 4.55, 4.60, 4.65, 4.70, 4.75, 4.80, 4.85, 4.90, 4.95, and/or 5.0 mg/mL.

In various embodiments, remineralization of teeth is from about 10 to about 99%. In some embodiments, remineralization of teeth is from about 30 to about 70% or from about 40 to 60%. In some embodiments, remineralization of teeth is at 10, 15, 20, 25, 30, 35, 40, 45, 50, 55, 60, 65, 70, 75, 80, 85, 90, 95 or 99%.

In various embodiments, the composition reduces previous tooth decay by from about 10 to about 99%. In some embodiments, the composition reduces previous tooth decay by 10, 15, 20, 25, 30, 35, 40, 45, 50, 55, 60, 65, 70, 75, 80, 85, 90, 95 or 99%.

EXAMPLES

Reference will now be made in detail to certain embodiments of the invention. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims. The headings below are not meant to limit the disclosure in any way; embodiments under any one heading may be used in conjunction with embodiments under any other heading.

Example 1: Preparation of Hybrid Chitosan/Amorphous Calcium Phosphate (CS-ACP) Powder The preparation of hybrid chitosan-amorphous calcium phosphate with co-precipitation methods are provided. Hybrid chitosan-amorphous calcium phosphate was prepared. Briefly, 10 mL of $CaCl_2$ and 15 mL $K_3PO_4$ containing 1.7% chitosan (MW 5K, International Laboratory USA) were mixed at a Ca/P molar ratio of 1.5 and under stirring. Precipitations were collected by filtration, washed with 30 mL of 2% ammonium, 40 mL 100% ethanol, and dried under vacuum. The formation of ACP was confirmed by Powder X-ray Diffraction (XRD) as shown in FIG. 1.

Example 2: Remineralization Effect of Amorphous Calcium Phosphate

Studies were conducted to determine the ability of ACP of Example 1 to facilitate the remineralization process in teeth.

Figure 2:
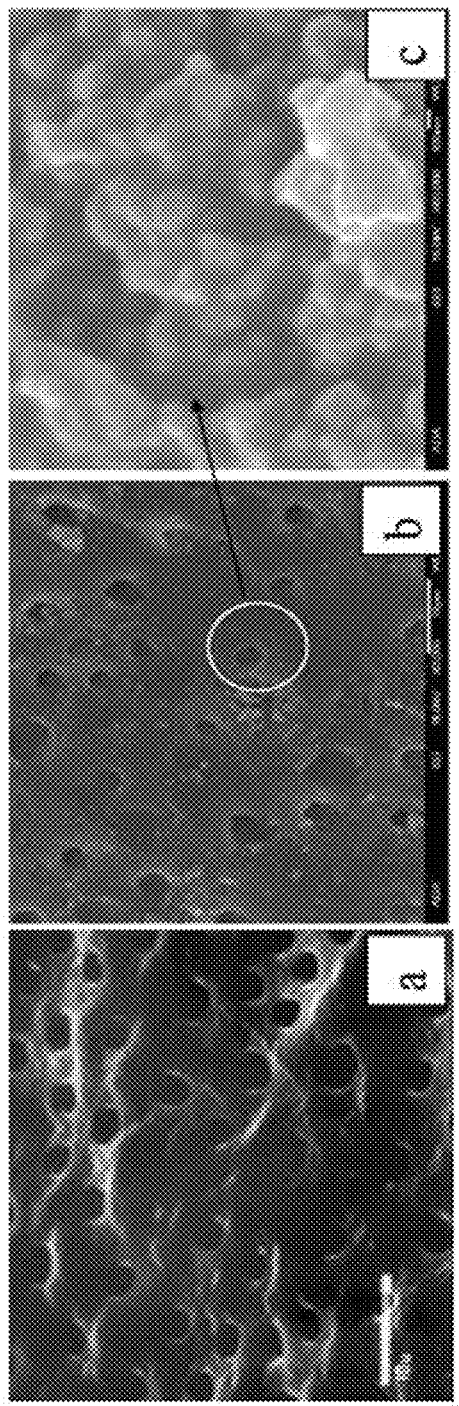
FIG. 2 illustrates the scanning electron microscope images of dentin surfaces before and after treatment with amorphous calcium phosphate.

The remineralization effect of ACP is shown in FIG. 2. Extracted molars were subjected to remineralization using ACP. The untreated etched surface of the molar is shown in FIG. 2 in image a. The treatment of ACP effectively reduced the size of dentin tubules (FIG. 2, image b). FIG. 2 image c shows high magnification of the precipitate showing nano-aggregates.

Example 3: Antimicrobial Activity of Chitosan

Figure 3:
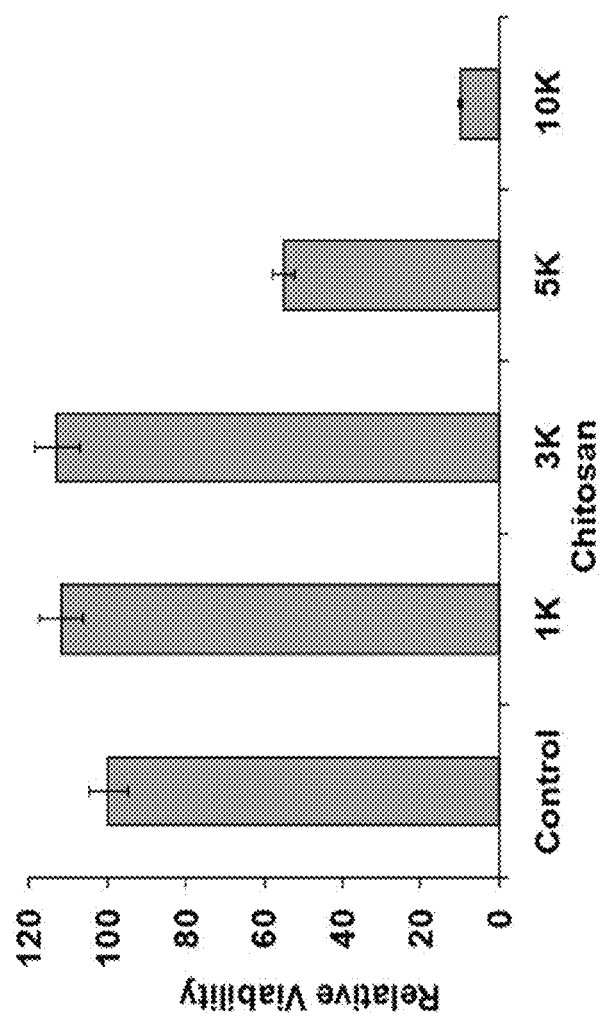
FIG. 3 depicts the antimicrobial effects of different molecular weights of chitosan on bacteria.

Chitosan is a known antimicrobial. The antimicrobial activities of chitosans were determined with XTT assay based on the measurement of bacterial metabolic activities. The bacteria include S. sanguis, S. fecalis, and S. mutans. The chitosan had an average molecular weight of 1K, 3K, 5K, and 10K. The metabolic activity and viability of S. mutans was decreased with the increase of the molecular weight of chitosan from 1K to 10K, as shown in FIG. 3. Chitosan with 10K molecular weight showed the greatest effect on inhibiting S. mutans metabolic activity. The relative viability of S. mutans treated with chitosan 10K was only about 10% as compared to the control. Chitosan with 5K molecular weight had a moderate inhibition effect with a relative viability of 55% as compared to the control. There was no significant antimicrobial effect for chitosan with a molecular weight of 1K and 3K. The antimicrobial properties of chitosan are related to their molecular weight, higher molecular weight chitosans exhibited better antimicrobial properties. The chitosan with molecular weight of 10K reached the greatest inhibition effect against S. mutans in our XTT assay.

Example 4: Antimicrobial Activity of Chitosan 10K on Different Oral Bacteria

Figure 4:
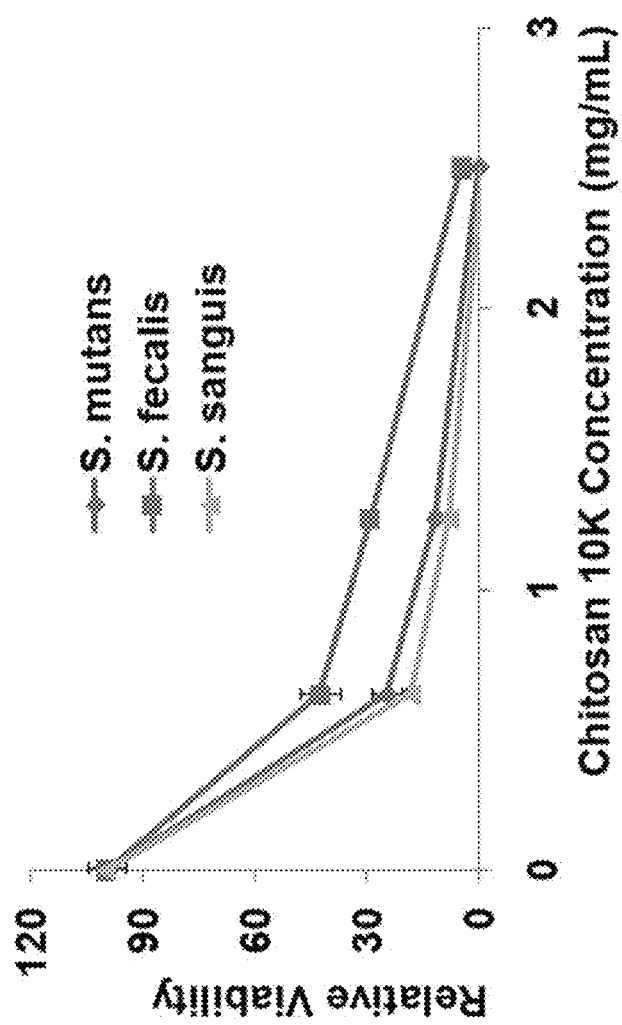
FIG. 4 illustrates the antimicrobial effects of a 10 kilodalton chitosan on different oral bacteria.

The antimicrobial activity of chitosan 10K was tested on three different oral bacteria which are major bacteria responsible for the occurrence of dental caries. As indicated in FIG. 4, chitosan 10K showed a significant inhibition of S. mutans, S. fecalus, and S. sanguis. The antimicrobial effects are concentration dependent and increased with increased chitosan concentration. Chitosan 10K was most active in the inhibition of S. sanguis ($IC_{50}$=0.623 mg/mL), followed by S. mutans ($IC_{50}$=0.655 mg/mL), and S. fecalus ($IC_{50}$=0.986 mg/mL).

Example 5: Preparation, Optimization, and Characterization of Toothpaste Containing Chitosan-Amorphous Calcium Phosphate To enhance the delivery of calcium and phosphate ions, we propose to prepare a toothpaste containing ACP, which is a bioactive form of Ca—P. Calcium salts and Phosphate will be encapsulated separately in different kinds of chitosan microsphere with a spray-drying method to generate in situ chitosan-ACP microspheres. Calcium and phosphate will be quickly released from chitosan microspheres in use, and form ACP in situ. This will increase the bioavailability of calcium and phosphate. Chitosan will further improve the efficiency by increasing the retention time of ACP. Chitosan functions as a delivery carrier and also works as an antimicrobial agent. Since $Ca^{2+}$ and $PO_4^{3-}$ are separated by encapsulating in different kinds of chitosan microspheres, this delivery system only forms ACP on use when tooth brushing activates the formation of ACP. The toothpaste prevents the premature conversion of ACP to HA during storage and thus results in significantly improved stability and prolonged product shelf-life. In this specific aim, we will prepare a novel, multifunctional toothpaste containing hybrid CS-ACP microspheres.

Preparation and Characterization of CS-ACP Microspheres

Preparation of CS-ACP Microspheres

In this method, we will prepare two types of chitosan microspheres containing calcium chloride and sodium phosphate, respectively, by spray-drying method. A chitosan solution containing calcium chloride and sodium phosphate will be prepared. The solutions will be spray-dried with a Büchi-B 190 spray dryer with a 0.7 mm fluid pressurized atomizer. Water and volatile acids in the solution will be removed with the air flow while the fine particles suspended in the air flow will be collected. Parameters such as feed rate, inlet temperature, atomizing air flow rate will be optimized to controlling the properties of CS-ACP microspheres. The prepared chitosan-calcium chloride and chitosan-sodium phosphate microspheres will be mixed at a Ca:P molar ratio of 1.5. These mixed microspheres will form ACP in situ when dissolved in water.

Characterization of CS-ACP Microspheres (a) Particle Size Analysis.

The particle size of microspheres will be determined by laser light diffraction after making a microsphere suspension in anhydrous ethanol.

(b) Calcium and Phosphate Release Profile.

Chitosan microspheres will be suspended in saline at a pre-determined time. Samples will be collected and the concentrations of calcium and phosphate in release medium will be determined with colorimetric assay kit (Biovision Inc, CA).

(c) Powder X-Ray Diffraction (XRD).

The formation of ACP will be confirmed with powder XRD. In situ ACP forming chitosan microspheres will be mixed with saline and precipitation will be collected, dried, and analyzed by XRD to confirm the formation of ACP.

Preparation of Toothpaste Containing CS-ACP

A standard tooth paste without any active ingredient (such as fluoride) will be dried under vacuum as base formula. ACP tooth paste will be prepared by mixing dried base formula toothpaste with in situ ACP forming chitosan microspheres and appropriate amount of glycerol. A colorimeteric assay kit will be used to assess the calcium and phosphate release profile.

Successful preparation of two types of CS-ACP microspheres and development of toothpaste is expected. Selection of appropriate concentration of chitosan, calcium salts, and phosphate salts and optimized feed rate for formation of optimal particle size will be the key to successful development of the CS-ACP toothpaste.

Example 6: Functional Assessment of CS-ACP-Based Toothpaste

1. Antimicrobial Testing

In our preliminary study, we have investigated the antimicrobial effects of chitosan with XTT assay. In this aim, we will determine the relative susceptibility of the oral microorganisms to chitosan with additional assays including XTT, zone of inhibition, and log reduction tests.

1.1 XTT Assay. The XTT assays will be repeated to determine the metabolic activities of bacteria. The bacteria include S. fecalis, S. mutans, and S. sanguis. Chitosan 10K will be used for the test. The effects of concentration and treatment time on bacteria metabolic activities will be determined with the XTT assay.

1.2 Zone of Inhibition. The zone of inhibition is utilized to measure the effect of chitosan against oral bacteria growth in culture. The bacteria are swabbed uniformly across a culture plate. A filter-paper disk, impregnated with the compound to be tested, is then placed on the surface of the agar. The compound diffuses from the filter paper into the agar. The concentration of the compound will be highest next to the disk, and will decrease as distance from the disk increases. If the compound is effective against bacteria at a certain concentration, no colonies will grow where the concentration in the agar is greater than or equal to the effective concentration. Thus, the size of the zone of inhibition is a measure of the compound's effectiveness: the larger the clear area around the filter disk, the more effective the compound.

1.3 Log Reduction. Log reduction test will be carried out against *S. fecalis, S. mutans*, and *S. sanguis*. This test is used to measure the killing ability of chitosan. A suspension of the test organism containing approximately 104 CFU/mL will be prepared by harvesting, and serially diluting in MRD. Six replicates of each test sample were placed into 24 well sterile tissue culture plates. Each well will be inoculated with 3 mL of the culture suspension and a 1mL sample immediately removed to provide time 0 baseline counts and leave 2 mL culture remaining in each well. Plates will then be sealed with parafilm and incubated at 37° C. with agitation at 150 rpm for 24 hours before enumeration. Viable counts will be determined after 0, 4, 8, 12, 24 h by plating serial dilutions of broth samples on pre-poured plate count agar (Difco Laboratories, Detroit, Mich.). Plates will be incubated at 35° C., and colonies were counted after 48 h of incubation by using a Quebec colony counter (American Optical Corp.).

1.4 Inhibition of Oral Biofilm Formation. Hydroxyapatite (HA) discs coated with whole human saliva will be incubated with ATCC strains of *S. mutans* 31377 and then will be divided into two groups: PBS control and chitosan 10K group. After 7-day incubation, biofilm mass will be collected. The number of colonized bacterial cells will be determined by XTT viability assay and also by dry weight of the biofilm present on each disc. All assays will be done in triplicate and will be repeated for three times.

The antimicrobial property of chitosan was well known and demonstrated in previous studies. (Rabea, E. I., Badawy, M. E., Stevens, C. V., Smagghe, G. & Steurbaut, W. Chitosan as antimicrobial agent: applications and mode of action. Biomacromolecules 4, 1457-1465 (2003).) Devlieghere, F., Vermeulen, A. & Debevere, J. Chitosan: antimicrobial lactivity, interactions with food components and applicability as a coating on fruit and vegetables. Food Microbiology 21, 703-714 (2004).)

Our preliminary results of XTT assay clearly indicated an effective inhibition effect of chitosan with MW 5K and 10K (FIGS. 3 and 4). The effective antimicrobial property of chitosan is beneficial for caries prevention. In Phase I study, besides XTT assay and zone of inhibition, we will also measure the killing ability of chitosan by using a log reduction test which will give us a full spectrum of the antimicrobial property of chitosan, which will help us optimize the chitosan concentration in the toothpaste formulation.

2 Demineralization/Remineralization Tests 2.1 In Vitro pH Cycling Model for Anti-Demineralization Assessment To conduct demineralization/remineralization tests, the Featherstone laboratory pH cycling model which have been multisite validated and been used extensively for over 20 years as an efficient, effective and reproducible means will be used to study the anti-caries potential of toothpaste formulations. (Stookey, G. K. et al. The Featherstone laboratory pH cycling model: a prospective, multi-site validation exercise. *Am J Dent* 24, 322-328 (2011). A similar pH cycling model has been used previously for the study of fluoride varnish on de/remineralization. (Hong, L., Ettinger, R. L., Watkins, C. A. & Wefel, J. S. In vitro evaluation of fluoride varnish on overdenture abutments. *J Prosthet Dent* 89, 28-36 (2003). Hong, L., Watkins, C. A., Ettinger, R. L. & Wefel, J. S. Effect of topical fluoride and fluoride varnish on in vitro root surface lesions. *Am J Dent* 18, 182-187 (2005).

Forty extracted human third molars will be randomly selected. Only those with sound, intact surface will be selected. Two layers of an acid resistant nail polish are painted on all surfaces except for a window (2×4 mm) on each tooth. Dental floss will be tied to a bur hole drilled in the root tip to allow suspension of the tooth in the various solutions. Early caries lesions will be created in vitro using a demineralization solution. Recaldent® CPP-ACP (MI paste, GC America, Alsip, Ill.) and calcium sodium phosphosilicate (SootheRx Toothpaste, 3M ESPE West Palm Beach, Fla.) will be used as positive controls since these two products are the remineralizing agent currently available in market for clinic use.

The teeth will be randomly divided into four groups: negative control, MI paste group, SootheRx group, and chitosan-ACP group. The treatment assignment is as follows:

Group A: Negative Control, no treatment except washed with distilled and deionized water for 20 seconds, therefore serve as negative controls.

Group B: MI paste, twice a day using a cotton swab to apply to tooth surface leaving undisturbed for 2 minutes.

Group C: SootheRx Toothpaste, twice a day using a regular toothbrush to brush tooth surface for 2 minutes.

Group D: Chitosan-ACP pre-prototype toothpaste, twice a day using a regular toothbrush to brush tooth surface for 2 minutes.

After first treatment according to group assignment, tooth specimen will be washed with deionized/distilled water for 20 seconds and placed in demineralizing solution for 6 hours, with purpose to form artificial caries-like lesions. The demineralization solution contains 2.2 mM/L $CaCl_2.2H_2O$, 2.2 mM/L $KH_2PO_4$ and 50 mM/L acetic acid at pH 4.3. After 6 hours, the specimens are retrieved, and washed in deionized/distilled water for 20 seconds. All specimens are then treated once more with respective treatment according to group assignment. After second treatment, all specimens will be placed in an artificial saliva solution for 17 hours. The artificial saliva solution contains 1.5 mM/L $CaCl_2.2H_2O$, 0.9 mM/L $KH_2PO_4$, and 150 mM/L KCl at pH 7.0. After 17 hours, the specimens are washed with deionized/distilled water for 20 seconds. This pH cycling is used to mimic the changes in the oral environment associated with food intake. This cycle is maintained continuously for 14 days.

3 Characterization and Data Analysis

We will use contemporary instrumental analysis techniques to characterize tooth surface, including morphological, chemical and mechanical analyses. Morphological assessment includes scanning electron microscopy (SEM) and polarized light microscopy (PLM). Lesion depth and remineralization band width will be measured from the PLM and μCT. Mineral density will also be measured using μCT. Conventional microindentation is an excellent tool to characterize the surface hardness and strength, especially for thin or thick films. In this project, we will use the conventional indentation with relatively large load to characterize surface hardness. Chemical analyses will include Auger Electron Spectroscopy and XPS to measure depth profile of calcium and phosphate.

Demineralization depth and remineralization width will be compared among 4 groups using the ANOVA. Data obtained from demineralization depth and remineralization width, chemical analysis, and mechanical analysis managed in the SPSS statistical program and the difference will be assessed among 4 groups using the ANOVA test.

Example 7: Chitosan/$CaCl_2$/$Na_2HPO_4$ for In-Situ Formation of Amorphous Calcium Phosphate (ACP) for Dental Remineralization 1. Synthesis of $CaCl_2$ or $Na_2HPO_4$ loaded chitosan microspheres.

10 K chitosan was dissolved in double distilled (DD) water at 80 mg/ml. The resulting mixture was centrifuged or filtered to remove any un-dissolved residuals to obtain the working chitosan solution. Acetic acid can be additionally added at 1 v % to dissolve the chitosan. $CaCl_2$ was dissolved in DD water at 1 M to prepare working $CaCl_2$ solution, and $Na_2HPO_4$ was dissolved in DD water at 0.667 M to prepare working $Na_2HPO_4$ solution, respectively.

For synthesis of chitosan/$CaCl_2$ microspheres, 1 ml of 10 K chitosan solution prepared above was mixed with 0.2 ml of $CaCl_2$ solution via vortexing for 2 minutes. The resulting solution was added into 10 ml of light mineral oil containing 100 mg of surfactant Span 80. The mixture was vortexed for 3 minutes at high speed to form milky water-in-oil emulsions. The resulting water-in-oil emulsion was then added to a 100 ml beaker which was on a hot/stirrer plate. Water was removed via evaporation by maintaining the temperature of the emulsion at 38° C. overnight (~19 hours) with a magnetic stirring speed of 400 RPM. The turbid mixture was then added into 80 ml of hexane to precipitate down the resulting chitosan/$CaCl_2$ microspheres. After centrifugation, the liquid was decanted. The precipitants were washed using 40 ml of hexane again and centrifuged to remove residual surfactants. The upper liquid was decanted after centrifugation. The washing and centrifugation were repeated twice. The final dry chitosan/$CaCl_2$ microspheres were obtained after vacuum drying and the resulting precipitants were obtained. The yield was 85~95 wt. The loading content of $CaCl_2$ was 14~16.6 wt % and was determined using a $Ca^{2+}$ ion selective electrode.

Alternatively, 10 ml of 10 K chitosan solution was prepared above and was mixed with 2 ml of $CaCl_2$ solution via vortexing for 2 minutes. The resulting solution was added into 120 ml of light mineral oil containing 1200 mg of surfactant Span 80 in a 250 ml beaker. The mixture was magnetically stirred at 1000 RPM for 30 minutes and then stirred at 750 RMP for 3 hours to form a milky water-in-oil emulsion. The resulting water-in-oil emulsion was then added to a 1000 ml beaker which was on a hot/stirrer plate. Water was removed via evaporation by maintaining the temperature of the emulsion at 38° C. overnight (~19 hours) followed by at 45° C. for 2-5 hours with a magnetic stirring speed of 500 RPM. The turbid mixture was then added into 400 ml of hexane to precipitate down the resulting chitosan/$CaCl_2$ microspheres. After centrifugation, the liquid was decanted. The precipitants were washed using 80 ml of hexane again and centrifuged to remove residual surfactants. The processes of washing and centrifugation were repeated twice. Final dry chitosan/$CaCl_2$ microspheres were obtained after vacuum drying the resulting precipitants. The yield was 85~95 wt %. The loading content of $CaCl_2$ was 14~16 wt % and was determined using a $Ca^{2+}$ ion selective electrode.

For synthesis of chitosan/$Na_2HPO_4$ microspheres, 1 ml of 10 K chitosan solution was prepared above and was mixed with 0.2 ml of $Na_2HPO_4$ solution via vortexing for 2 minutes. The resulting solution was added into 10 ml of light mineral oil containing 100 mg of surfactant Span 80. The mixture was vortexed for 3 minutes at high speed to a form milky water-in-oil emulsion. The resulting water-in-oil emulsion was then added to a 100 ml beaker which was on a hot/stirrer plate. Water was removed via evaporation by maintaining the temperature of the emulsion at 38° C. overnight (~19 hours) with a magnetic stirring speed of 400 RPM. The turbid mixture was then added into 80 ml of hexane to precipitate down the resulting chitosan/$Na_2HPO_4$ microspheres. After centrifugation, the liquid was decanted. The precipitants were washed using 40 ml of hexane and centrifuged to remove residual surfactants. The washing and centrifugation were repeated twice. Final dry chitosan/$Na_2HPO_4$ microspheres were obtained after vacuum drying the resulting precipitants. The yield was 81~85 wt %. The loading content of $Na_2HPO_4$ was 22~23 wt % and was determined using an Abeam® phosphate assay kit (colorimetric).

Alternatively, 10 ml of 10 K chitosan solution was prepared above and was mixed with 2 ml of $Na_2HPO_4$ solution via vortexing for 2 minutes. The resulting solution was added into 120 ml of light mineral oil containing 1200 mg of surfactant Span 80 in a 250 ml beaker. The mixture was magnetically stirred at 650 RPM for 3 hours to form a milky water-in-oil emulsion. The resulting water-in-oil emulsion was then added to a 1000 ml beaker which was on a hot/stirrer plate. Water was removed via evaporation by maintaining the temperature of the emulsion at 38° C. for overnight (~19 hours) followed by at 45° C. for 2-5 hours with a magnetic stirring speed of 500 RPM. The turbid mixture was then added into 400 ml of hexane to precipitate down the resulting chitosan/$Na_2HPO_4$ microspheres. After centrifugation, the liquid was decanted. The precipitants were washed using 80 ml of hexane again and centrifuged to remove residual surfactants. The washing and centrifugation were repeated twice. Final dry chitosan/$Na_2HPO_4$ microspheres were obtained after vacuum drying the resulting precipitants. The yield was 81~85 wt %. The loading content of $Na_2HPO_4$ was 22~23 wt % and was determined using an Abeam® phosphate assay kit (colorimetric).

2. The Release of Calcium Ions or Phosphate Ions from the Chitosan Microspheres.

Figure 5:
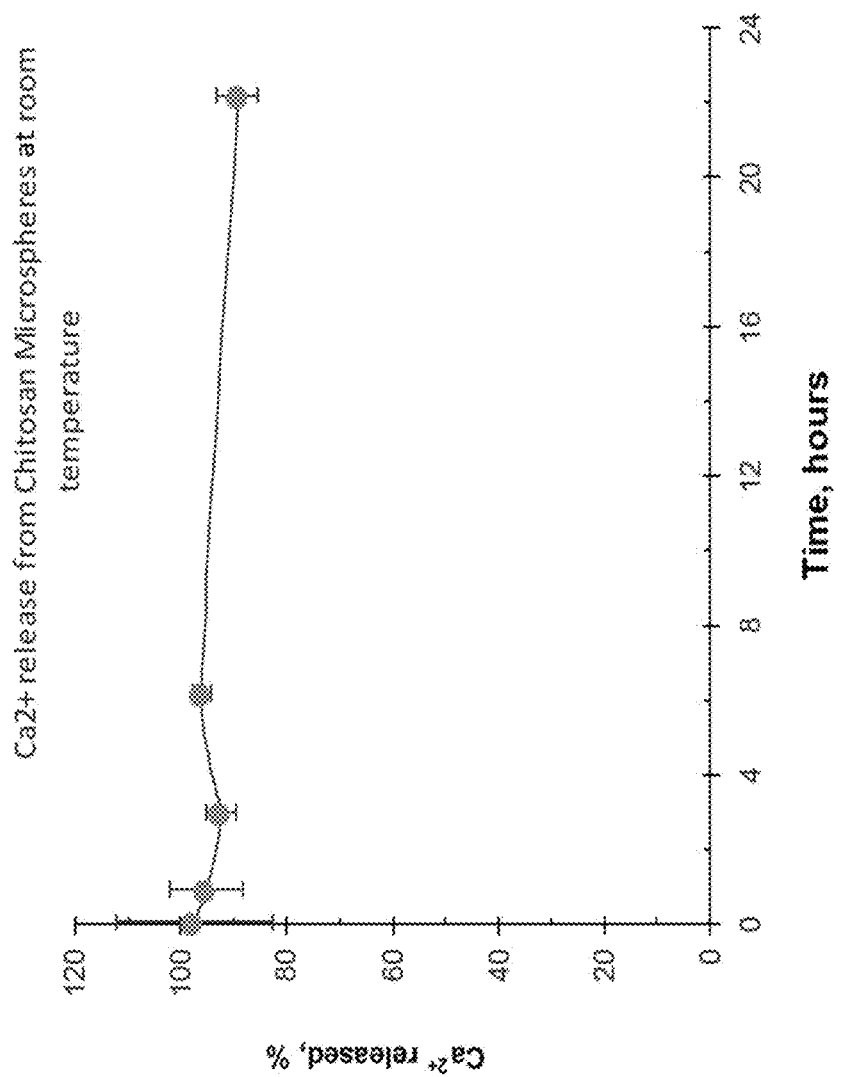
FIG. 5 depicts release of $Ca^{2+}$ from chitosan/$CaCl_2$ microspheres at room temperature.

Release of calcium or phosphate ions was conducted at room temperature with DD water as the release medium. The release medium was sampled at 5 minutes, 55 minutes, 3 hours, 6 hours 10 minutes, and 22 hours 10 minutes. After samples were properly processed, the calcium or phosphate concentrations were determined using a $Ca^{2+}$ ion selective electrode or an Abeam® phosphate assay kit (colorimetric), according to the manufacturer's instructions, respectively. FIG. 5 shows a typical release profile for $Ca^{2+}$ release from chitosan/$CaCl_2$ microspheres prepared in section 1 using the 10 K chitosan. The release is very fast, almost instantly, with about 97% of loaded $Ca^{2+}$ released within 5 minutes. To achieve longer release of $Ca^{2+}$, less water soluble calcium salts could be used and less hydrophilic polymer might be mixed with chitosan to synthesize the microspheres.

Figure 6:
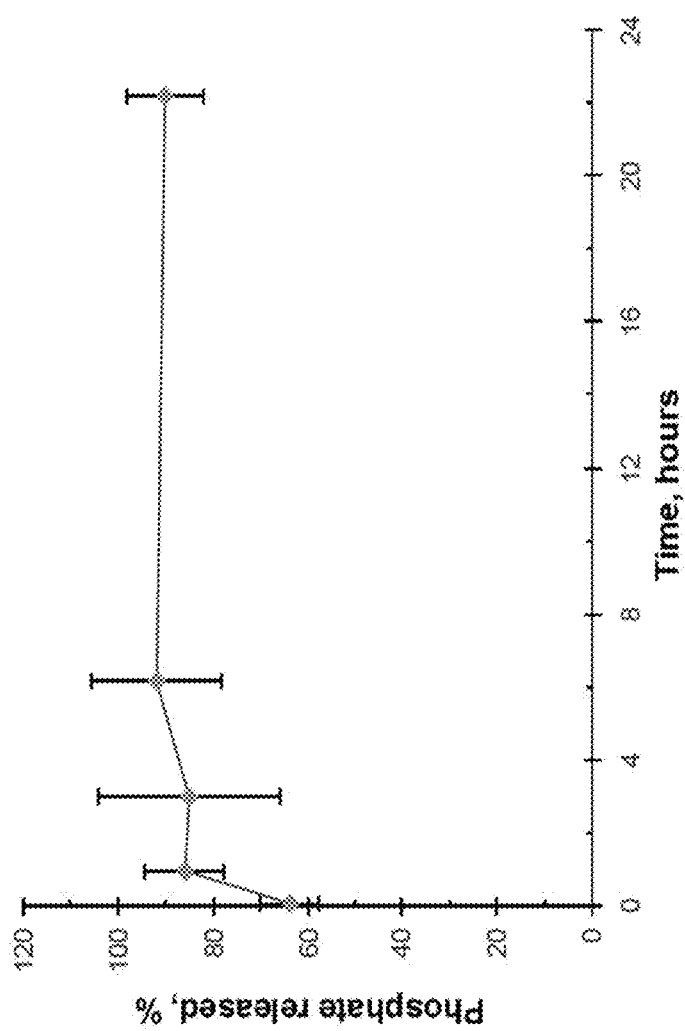
FIG. 6 illustrates a typical release profile for phosphate release from chitosan/$Na_2HPO_4$ microspheres prepared using the 10 K chitosan.

FIG. 6 shows a typical release profile for phosphate release from chitosan/$Na_2HPO_4$ microspheres prepared in section 1 using the 10 K chitosan. The release is fast with more than 63% released at 5 minutes and about 85% within 190 minutes. To achieve longer release of phosphate, less water soluble phosphate salts could be used and less hydrophilic polymer might be mixed with chitosan to synthesize the microspheres. The release of the phosphate ions from chitosan/$Na_2HPO_4$ microspheres was at room temperature. The pH of the release medium was monitored during the release course for both chitosan microspheres.

Figure 7:
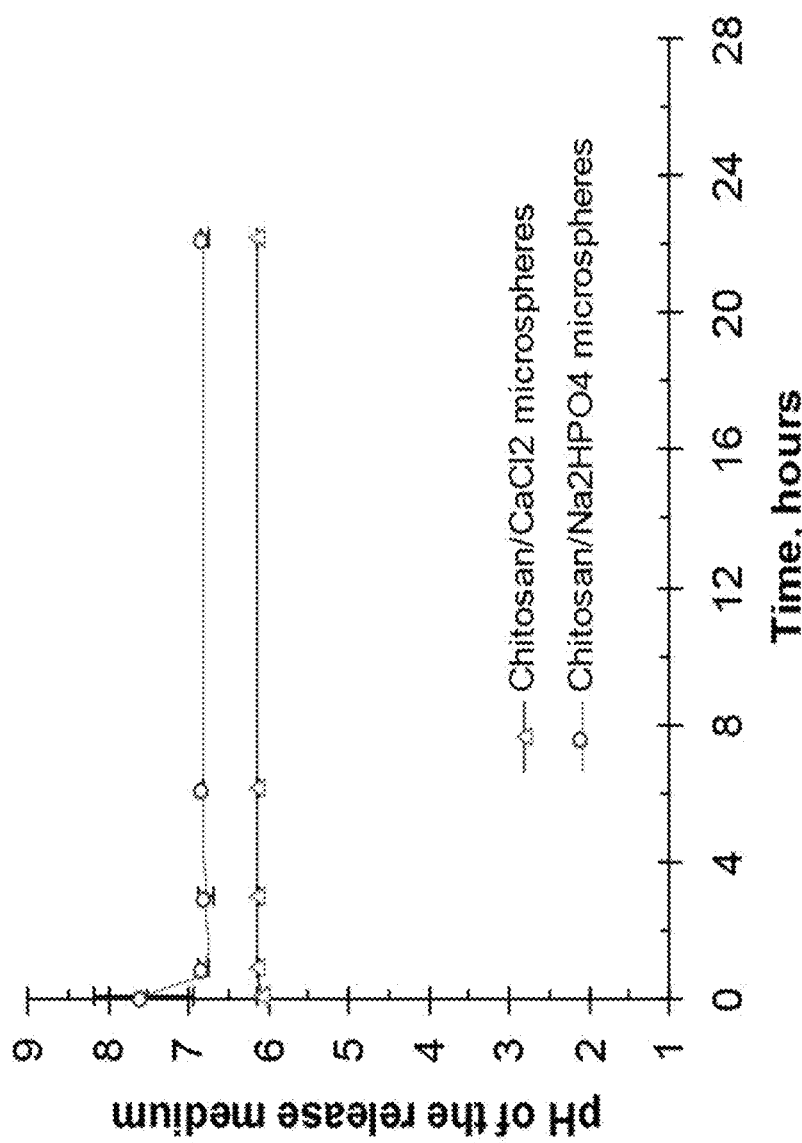
FIG. 7 depicts the pH of the release medium for the two microspheres during the release course.

FIG. 7 shows the pH change during the release course for the release medium. The double distilled water had neutral pH. For chitosan/$CaCl_2$ microspheres, the pH remained relative stable at ~6.1 from the first sampling time point of 5 minutes to the last point of 22 hours 10 minutes. While, for chitosan/$Na_2HPO_4$ microspheres, the pH dropped from 7.56 at 5 minutes to 6.81 at 55 minutes, and afterwards it remained relative stable at 6.8. To enable the chitosan to have the capability to partially neutralize the acidic environment caused by oral bacteria, arginine will be added into the final paste formulation. Arginine is a stronger base than chitosan. The addition of arginine will generate the free base form of chitosan since acid is always used to facilitate the dissolution of chitosan in water otherwise chitosan is not soluble in water at neutral pH. The addition of arginine will also bring other benefits such as facilitating the formation of ACP. Once the free base chitosan is positively charged again, it will demonstrate an anti-bacterial property again.

3. The FT-IR Spectra of Chitosan Microspheres.

Figure 8:
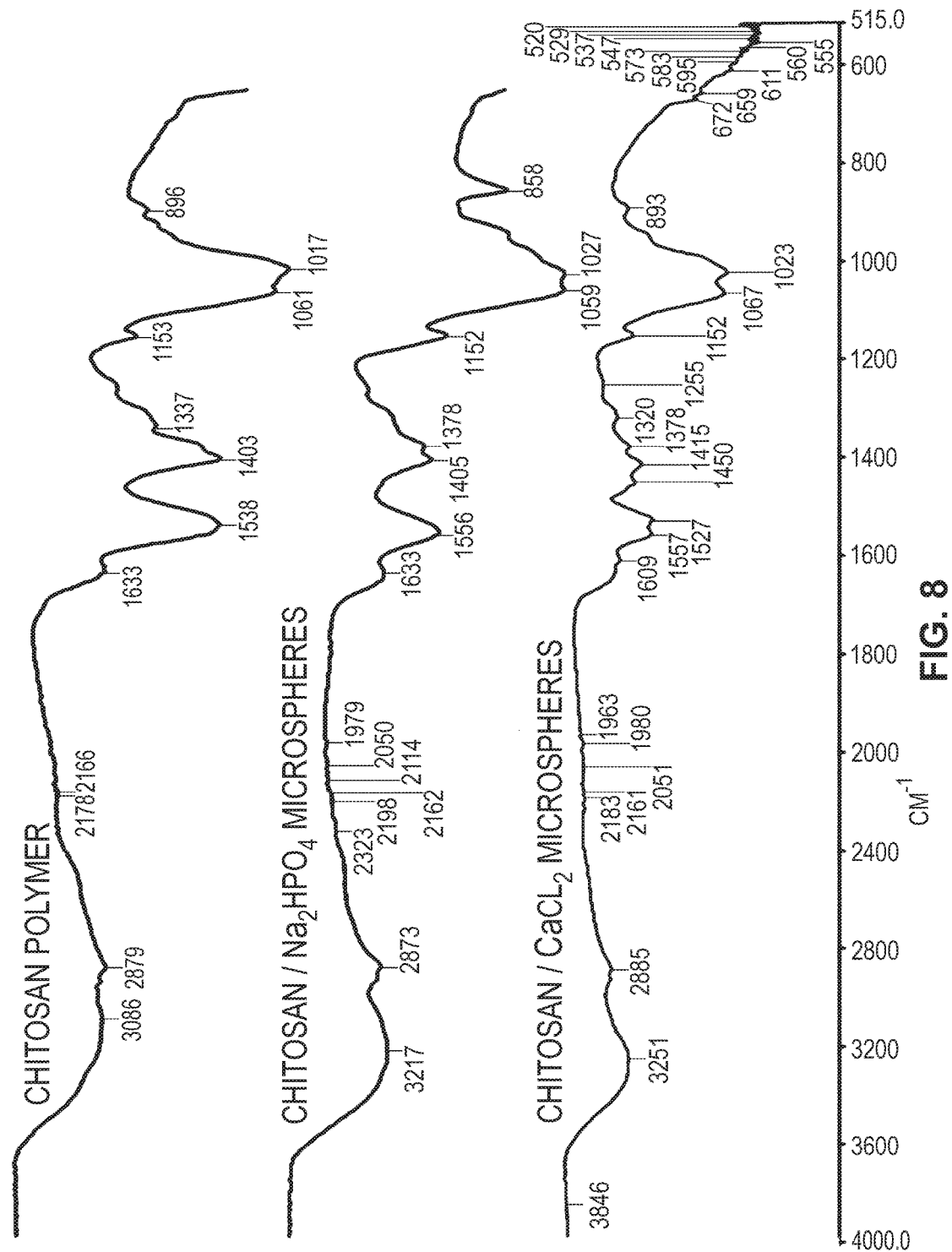
FIG. 8 illustrates FT-IR spectra of 10 k chitosan, chitosan/$Na_2HPO_4$ microspheres and chitosan/$CaCl_2$ microspheres.

The FT-IR spectra of the raw 10K chitosan, chitosan/$CaCl_2$ microspheres, and chitosan/$Na_2HPO_4$ microspheres were recorded using a FT-IR spectroscopy. FIG. 8 shows the typical FT-IR for 10K chitosan, chitosan/$CaCl_2$ microspheres, and chitosan/$Na_2HPO_4$ microspheres. 10K chitosan has the characteristic peaks of polysaccharides at 1153 $cm^{-1}$ (vC-O-C in the glycosidic bridges), 1061 $cm^{-1}$ (vC-0 near the primary hydroxyl groups) and 1017 $cm^{-1}$ (coupled vC-C and vC-O), and amide band I at 1633 $cm^{-1}$ and amide band II at 1538 $cm^{-1}$ due to N-acetyl groups. After incorporating $Na_2HPO_4$ into chitosan to form microspheres, in addition to the characteristic peaks observed for chitosan, two new peaks at 1378 $cm^{-1}$ and 858 $cm^{-1}$ were observed. The later peak is due to $HPO_4^{2-}$. After incorporating $CaCl_2$ into chitosan to form microspheres, in addition to the characteristic peaks observed for chitosan, several new peaks at 1527 $cm^{-1}$, 1450 $cm^{-1}$, and 1378 $cm^{-1}$ were observed. Additional salts which can be used:

| Chemical | Water Solubility |
| --- | --- |
| Calcium acetate | 34.7 g/100 mL (20° C.) |
| $CaCl_2$ | 81.1 g/100 mL (25° C.) |
| Calcium pantothenate | 50 mg/mL (25° C.) |
| Calcium ascorbate | 50 g/100 mL |
| Calcium gluconate | Slowly soluble, 4.33 g/100 mL |
| Calcium lactate | 7.9 g/100 mL (30° C.), 6.7 g/100 mL (25° C.) |
| Calcium acetylacetonate | |
| Calcium lactobionate | |
| Calcium citrate | 0.095 g/100 mL (25° C.) |
| Calcium α-D-heptagluconate | |
| Calcium benzoate | 2.72 g/100 mL (20° C.) |
| Saccharin calcium | |
| Sorbic acid calcium | |

Example 8: EDX Analysis of $CaCl_2$/Chitosan and $Na_2HPO_4$/Chitosan Microspheres Synthesized $CaCl_2$/chitosan and $Na_2HPO_4$/chitosan micro spheres were characterized using scanning electron microscopy (SEM). Briefly, $CaCl_2$/chitosan or $Na_2HPO_4$/chitosan microspheres were mounted on the SEM sample holder using carbon double-adhesive tape. Gold was sputtered on the surface of the sample. The gold-sputtered samples were observed using SEM.

Figure 9:
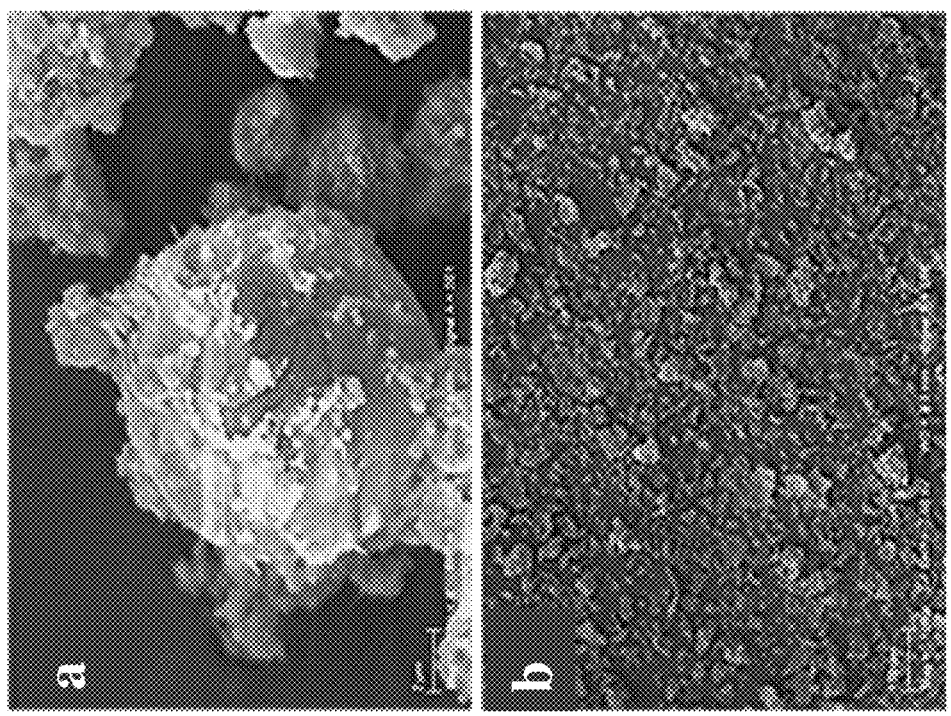
FIG. 9 illustrates SEM images scanned at 5,000× magnification shown in image a, and at 100× magnification shown in image b for as-synthesized $CaCl_2$-loaded chitosan microparticles.

FIG. 9 shows the typical SEM images for the synthesized $CaCl_2$/chitosan microspheres scanned at magnifications of 5,000×, and 100×. The microspheres were less definitive (FIG. 9, image a) with some nanostructures on the surface of micron-sized particles (less than 10 μm). EDX analysis showed that both those nanostructures and the micron-sized particles had calcium and nitrogen elements, indicating both $CaCl_2$ and chitosan were existing there and that they were prone to form aggregates less than 100 μm (FIG. 9, image b).

Figure 10:
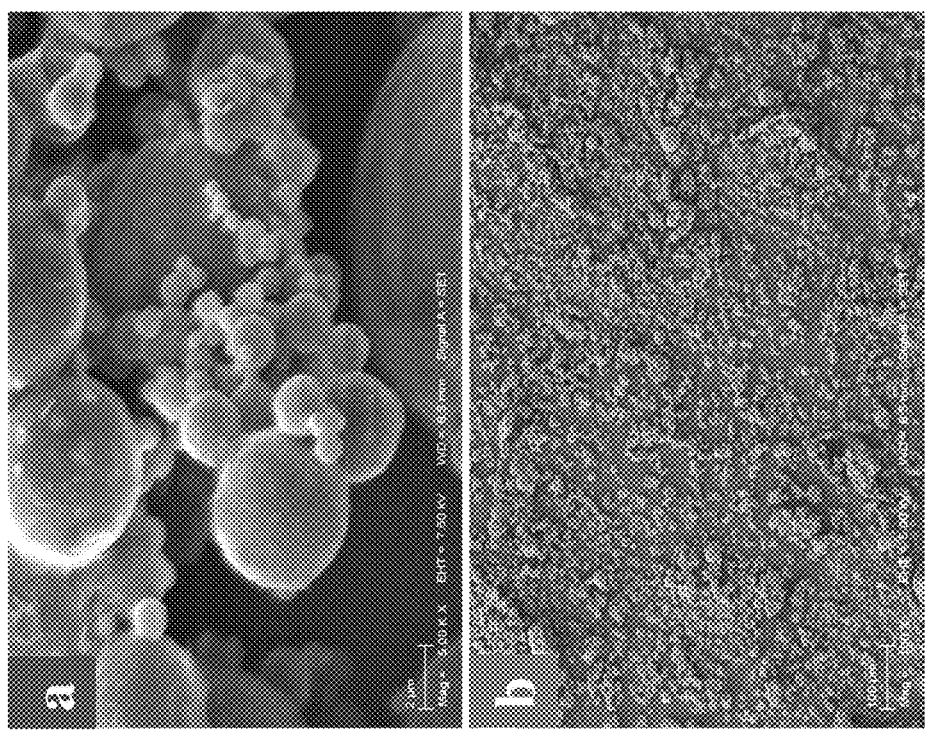
FIG. 10 illustrates SEM images scanned at 5,000× magnification shown in image a, and 100× magnification shown in image b for as-synthesized $Na_2HPO_4$-loaded chitosan microparticles.

FIG. 10 shows typical SEM images for the synthesized $Na_2HPO_4$/chitosan microspheres scanned at magnifications of 5,000× and 100×. The microspheres were well defined with particle size of less than 5 μm (FIG. 10, image a). EDX analysis showed that the micron-sized particles had sodium, phosphorus and nitrogen elements, indicating both $Na_2HPO_4$ and chitosan were existing there, and that they could form aggregates of less than 100 μm (FIG. 10, image b).

Figure 11:
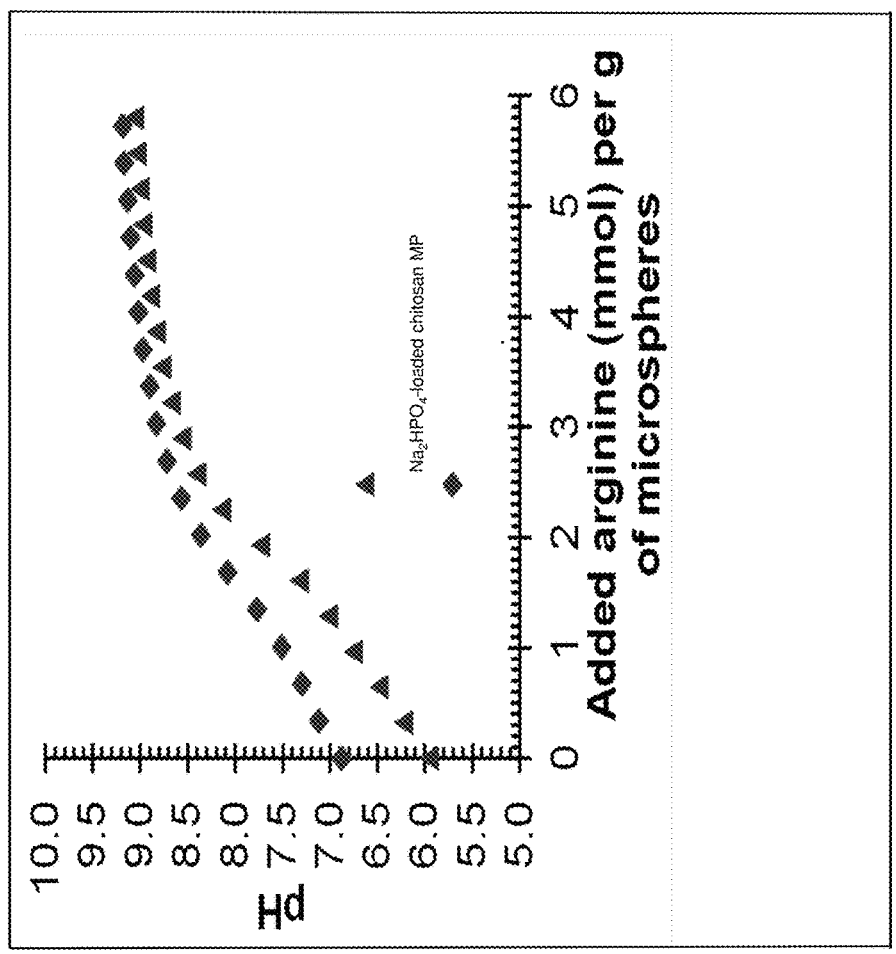
FIG. 11 illustrates the pH change of $CaCl_2$/chitosan and $NaHPO_4$/chitosan suspension with the addition of arginine solution at a pH of 9.6.

FIG. 11 showed the pH change of $CaCl_2$/chitosan or $Na_2HPO_4$/chitosan suspension with the addition of arginine solution (pH 9.6). With the addition of arginine, the pH was rapidly increased to around 8.3, and then gradually approach to around 9 below the pH 9.6 of the arginine solution used.

Example 9: Toothpaste Formulation Tested in De-/Re-Mineralization

A homogeneous viscous thickening mixture was prepared by mixing non-ionic thickener hydroxyethyl cellulose with glycerol/water co-solvents. The resulting aqueous mixture was lyophilized to remove the water, leaving a water-free viscous thickening mixture behind. Toothpaste was formulated right before use by mixing the $CaCl_2$/chitosan microspheres with the above viscous thickening mixture at a weight ratio of 15:85.

The College of Dentistry at the University of Tennessee Health Science Center has a large pool of disinfected human third molars extracted from dental patients due to daily clinical practice. The patient for each tooth could not be identified. The use of these de-identified teeth is exempt from the regulations of human subjects.

Sound human third molars were randomly selected from the pool mentioned above and painted with two layers of acid resistant nail polish on all surfaces except for a window (2×7 mm) for each tooth after cleaning. Dental floss was tied to a bur hole drilled in the root tip to allow suspension of the tooth in solution. The painted teeth were randomly divided into three groups (ten teeth per group): negative control (labeled as Contr), MI paste plus group (positive group, labeled as MI+), and experimental group (labeled as Chi-ACP). MI paste plus (Recaldent™ CPP-ACP, GC America) was used as positive control since it had been tested using the in vitro pH cycling model for remineralization of enamel subsurface lesions. Due to the 0.2% (900 ppm) fluoride in MI paste plus, the manufacturer does not recommend its use in children under 6 years old and for overnight application in children under 12 years old. MI paste plus might also cause allergies since it contains milk proteins and benzoate.

The Featherstone laboratory pH cycling model has been validated by multi-sites and used extensively for over 25 years as an efficient, effective and reproducible protocol for de-/re-mineralization testing. We used it to study the anti-caries potential of toothpaste formulations by assessing the gain/loss of enamel mineral. The in vitro pH cycling approach used in this work comprised of 15 demineralization stages with 6 hours per stage and 15 remineralization stages with 16.5 hours per stage (one demineralization followed by one remineralization per day). The demineralization solution contained 2.2 mM $CaCl_2$, 2.2 mM $KH_2PO_4$ and 50 mM acetic acid at pH 4.3. The remineralization solution contained 1.5 mM $CaCl_2$, 0.9 mM $KH_2PO_4$, and 150 mM KCl at pH 7.0. During the transition from demineralization solution to remineralization solution or from remineralization solution to demineralization solution, the teeth received a treatment as follows. The negative control group received no treatment except for washing with DD water for 60 seconds; MI paste plus group was treated with MI paste plus by using an application brush to apply a thin layer of MI paste plus on the exposed tooth surface window and then left undisturbed for 10 minutes according to the manufacturer's instruction; and the Chi-ACP group (i.e. experimental group) received tooth brushing by using an application brush to manually brush the exposed tooth surface window in the presence of a slurry of the selected toothpaste (~40 mg toothpaste and 150 μl $Na_2HPO_4$/arginine solution per tooth) for 1 minute. For all of the three groups the tooth specimen was washed with DD water for 60 seconds both before and after the treatments according to group assignment. The teeth were washed for 60 seconds every time when they were removed from the demineralization or remineralization solutions. After the treatments, the teeth were suspended in the corresponding demineralization solutions or remineralization solutions at room temperature.

After the 15 days of de-/re-mineralization, the teeth were first analyzed for the elemental compositions on the treated enamel surface using energy-dispersive x-ray detector (EDX) coupled to SEM. After the EDX analysis, the teeth were then sectioned buccolingually to 120-150 μm thick per section using hard tissue microtome to expose the cross sections beneath the treated enamel surfaces. These thin slides were observed under polarized light microscope (PLM).

The objective was to develop a novel toothpaste for anti-caries via in-situ formation of ACP from $Ca^{2+}$ and phosphate ions released from chitosan microspheres. To test this concept, we simplified the process by using $CaCl_2$/chitosan microspheres, and phosphate water which replaced the chitosan-phosphate microspheres. Thus, we formulated non-aqueous toothpaste containing $CaCl_2$/chitosan microspheres, hydroxyethyl cellulose and glycerol. This toothpaste was tested for remineralization of enamel along with negative control, and positive control MI paste plus. The experimental group was treated by brushing the exposed enamel window for 1 minute with this formulated toothpaste in combination with $Na_2HPO_4$ and arginine dissolved in DD water (labeled as Chi-ACP group in FIGS. 12 and 13) during the 15 days of de-/re-mineralization cycles.

Figure 12:
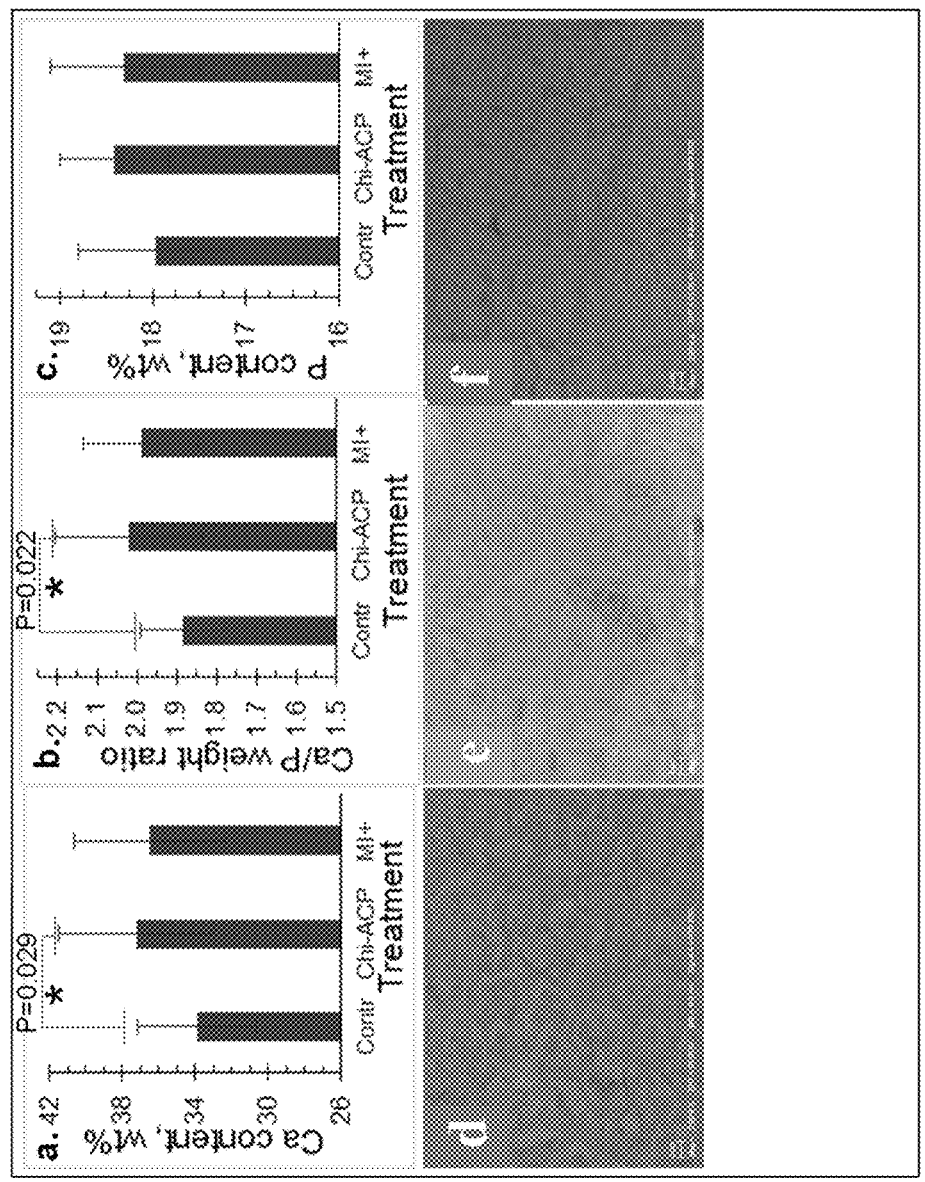
FIG. 12 illustrates results of elemental analysis for treated enamel surfaces for three groups including Contr, Chi-ACP and MI+. Compared with the negative control group (Contr group, treated with DD water), the Chi-ACP group had statistically significant increases in both Ca contents (37.23±4.25 wt % vs. 33.89±3.28 wt %) and Ca/P weight ratios (2.02±0.19 vs. 1.88±0.11) on the treated enamel surfaces (shown in images a and b). Meanwhile, the positive control group (MI+ group) treated with MI paste plus had some increases in both Ca content (36.51±4.14 wt % vs. 33.89±3.28 wt %) and Ca/P weight ratio (1.99±0.14 vs. 1.88±0.11). For all three tooth groups, the phosphate content slightly increased from 17.97±0.82 wt % for the negative control group, to 18.30±0.80 wt % for the positive control MI+ group, to 18.41±0.59 wt % for the experimental group Chi-ACP, although statistically no significant difference exists between any two groups (shown in image c). SEM was used to observe the surface morphology of treated enamel (shown in images d, e and f). For all three groups, no apparent deposits were observed.

FIG. 12 shows the results of elemental analysis for the treated enamel surfaces in all three groups. Compared with the negative control group (Contr group, treated with DD water), this Chi-ACP group had statistically significant increases in both Ca contents (37.23±4.25 wt % vs. 33.89±3.28 wt %) and Ca/P weight ratios (2.02±0.19 vs. 1.88±0.11) on the treated enamel surfaces (FIG. 12, images a and b). Meanwhile, the positive control group (i.e. MI+ group) treated with MI paste plus had some increases in both Ca content (36.51±4.14 wt % vs. 33.89±3.28 wt %) and Ca/P weight ratio (1.99±0.14 vs. 1.88±0.11), but the increases were not statistically significant at the level of p=0.05 (FIG. 12 images a and b). For all three tooth groups, the phosphate content slightly increased from 17.97±0.82 wt % for the negative control group, to 18.30±0.80 wt % for the positive control MI+ group, to 18.41±0.59 wt % for the experimental group Chi-ACP, although statistically no significant difference exists between any two groups (FIG. 12, image c). SEM was used to observe the surface morphology of treated enamel (FIG. 12, images d, e and f). For all three groups, no apparent deposits were observed. This observation was contrary to the observations in anti-hypersensitivity studies which found that it was always reported that the dentine tubular was occluded by deposits from toothpaste. But, most of those studies did not let the treated dentine be exposed to pH cycling and they were evaluated almost immediately after the treatments.

Figure 13:
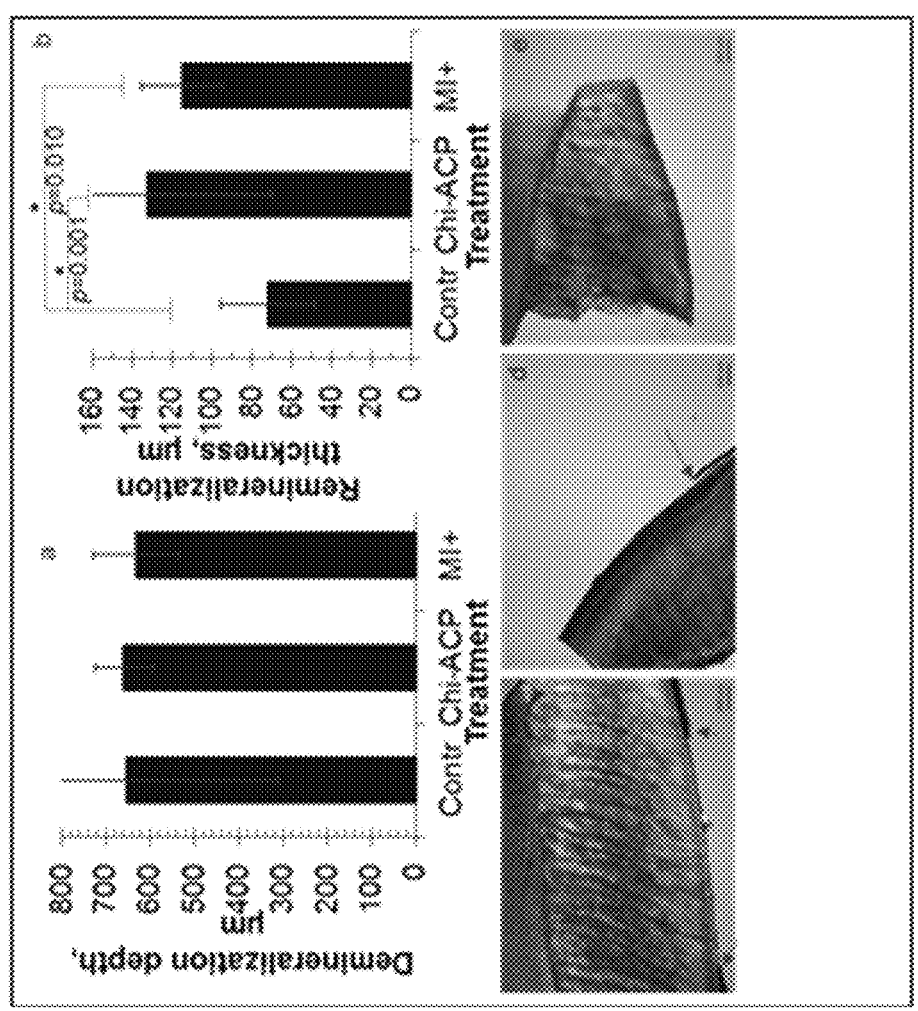
FIG. 13 illustrates the results of measuring demineralization depth and re-mineralization thickness under treated enamel surfaces by PLM. Image a depicts the average demineralization depth and image b depicts the remineralization thickness determined by PLM for enamels of the Contr group (image c), Chi-ACP group (image d) and MI+ group (image e).

We measured the demineralization depth and remineralization thickness under the treated enamel surface by PLM. For all three groups, there was no significant difference in the demineralization depth among the three groups and between any two groups. The demineralization fronts were penetrated at about 650 μm beneath the enamel surface. This was higher than our previous report of 400 μm. The reason for this difference was beyond the goal of this current investigation. However, the remineralization thicknesses for all three groups were statistically different as shown in FIG. 13. The negative control group (Contr groups) had the lowest remineralization thickness (73.8±24.9 μm), which was in accordance with our previous report. The experimental group (Chi-ACP group) had the highest remineralization thickness (131.4±63.6 μm), followed by positive group (MI+ group, 115.2±26.8 μm). The difference among the three groups was statistically significant at the level of p=0.05. A post hoc test (Dunnett's test) showed that there were statistically significant differences in remineralization depth between Contr and Chi-ACP groups or between Contr and MI+ groups at the level of p=0.05. Further analysis showed that no statistical difference existed between the Chi-ACP group and MI+ group on remineralization thickness, although Chi-ACP group had a slightly larger remineralization thickness than MI+ group. Due to the fact that MI paste plus contains 900 ppm fluoride, which was close the fluoride content used in regular fluorinated toothpaste, the developed toothpaste has apparent advantages over MI paste plus for remineralizing decayed enamels.

Example 10: Additional Toothpaste Formulations

Figure 14:
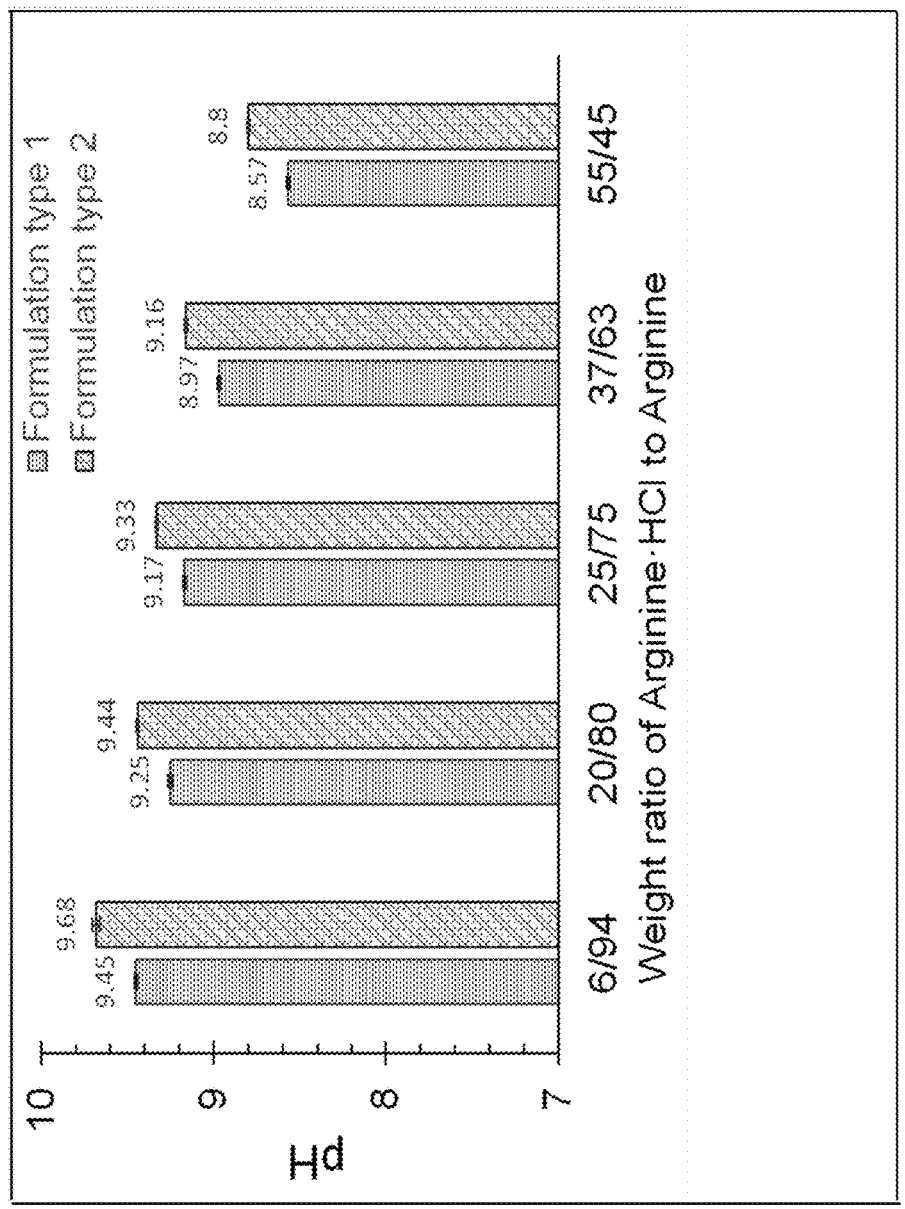
FIG. 14 illustrates results that show that adjusting the ratio of arginine•HCl to free base arginine changes the pH of two toothpaste formulations being tested.

We have formulated non-aqueous toothpaste containing chitosan microparticles (16.7 wt %, either $CaCl_2$ loaded or $Na_2HPO_4$ loaded), Poloxamer 124 (53.3 wt %), polyethylene glycol (PEG) (12.0 wt %), hydroxypropyl cellulose (HPC) (1.3 wt %) and arginine (16.7 wt %). By adjusting the weight ratio of an arginine hydrochloride salt (arginine•HCl) to free base arginine, the pH could be easily controlled in the range of 8.5 to 9.7 (FIG. 14). In other potential toothpastes, the content of chitosan will be in the range of 5 wt % to 18 wt %, while the content of $CaCl_2$ and $Na_2HPO_4$ will be less than 2 wt %. In particular, homogeneous viscous thickening mixtures will be prepared by first dissolving HPC in PEG, followed by adding Poloxamer 124 by varying their ratios. Toothpastes will be formulated by manual mixing chitosan microparticles with the above viscous thickening mixture at different ratios. Free base arginine and arginine•HCl will be added to adjust the pH of the prepared toothpastes accordingly (FIG. 14). Other ingredients such as titanium dioxide may be added into the toothpaste formulations to adjust the total content of the solids.

We are waiting for enough extracted human teeth for testing the efficacy of these secondary toothpaste formulations.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A composition for remineralizing teeth, the composition comprising a remineralizing agent consisting of a first set of chitosan microspheres consisting of chitosan and calcium, a second set of chitosan microspheres consisting of chitosan and phosphate, and arginine.

2. A composition of claim 1, wherein (i) the size of the microspheres are between 1 μm to 99 μm; (ii) the calcium is homogeneously dispersed or dissolved within the first set of chitosan microspheres; or (iii) the phosphate is homogeneously dispersed or dissolved within the second set of chitosan microspheres.

3. A composition of claim 1, wherein the microspheres consisting of chitosan and calcium and the microspheres consisting of chitosan and phosphate are mixed at a ratio of between about 1:1 to about 1:2 of calcium to phosphate.

4. A composition of claim 1, wherein the microspheres consisting of chitosan and calcium and the microspheres consisting of chitosan and phosphate release calcium and phosphate ions, respectively, and form amorphous calcium phosphate in situ in an aqueous environment in the oral cavity.

5. A composition of claim 1, wherein the composition is a toothpaste, gel, varnish, cream, sealant and/or chewing gum.

6. A composition of claim 1, wherein the composition comprises from about 1% to about 10% by weight calcium phosphate based on the total weight of the composition.

7. An antimicrobial composition of claim 1, wherein the chitosan has a molecular weight of 3 kilodaltons to 9 kilodaltons.

8. A composition of claim 1, wherein the calcium is calcium chloride and the phosphate is disodium phosphate.

9. A composition of claim 1, wherein the size of the microspheres are between 1 μm to 99 μm, the first set of chitosan microspheres comprise calcium chloride and the second set of microspheres comprise disodium phosphate, the calcium chloride and the disodium phosphate are each in an amount of less than 2 wt % of the composition, the molecular weight of the chitosan is 3 kilodaltons to 9 kilodaltons, and the chitosan is in an amount of about 5 to 18 wt % of the composition.

10. A composition of claim 1, wherein the first set of chitosan microspheres consist of calcium chloride and the second set of chitosan microspheres consist of disodium phosphate, the calcium chloride and the disodium phosphate are each in an amount of less than 2 wt % of the composition, the molecular weight of the chitosan is 3 kilodaltons to 9 kilodaltons, and the chitosan is in an amount of about 5 to 18 wt % of the composition.

11. A composition of claim 1, wherein the pH in a mouth of a patient is raised to 7.5 to about 9 when the composition is administered to the mouth.

12. A composition for remineralizing teeth, the composition comprising a remineralizing agent consisting of a first set of chitosan microspheres consisting of chitosan and calcium, a second set of chitosan microspheres consisting of chitosan and phosphate, and arginine, wherein the size of the microspheres are between 1 μm to 99 μm, the molecular weight of the chitosan is 3 kilodaltons to 9 kilodaltons, and the chitosan is in an amount of about 5 to 18 wt % of the composition.

* * * * *